United States Patent
Xie et al.

(10) Patent No.: US 6,951,864 B2
(45) Date of Patent: Oct. 4, 2005

(54) 4-IMIDAZOL-1-YLMETHYL-PYRIMIDINE DERIVATIVES

(75) Inventors: Linghong Xie, Guilford, CT (US);
Bingsong Han, Hamden, CT (US);
Yuelian Xu, East Haven, CT (US);
George D. Maynard, Clinton, CT (US)

(73) Assignee: Neurogen Corp., Branford, CT (US)

( * ) Notice: Subject to any disclaimer, the term of this patent is extended or adjusted under 35 U.S.C. 154(b) by 203 days.

(21) Appl. No.: 10/702,629

(22) Filed: Nov. 6, 2003

(65) Prior Publication Data

US 2004/0102457 A1 May 27, 2004

Related U.S. Application Data

(60) Provisional application No. 60/424,945, filed on Nov. 8, 2002.

(51) Int. Cl.[7] .................. C07D 403/06; A61K 31/4178
(52) U.S. Cl. .................. 514/255.05; 514/256; 544/333
(58) Field of Search .................. 544/333; 514/256, 514/255.05

(56) References Cited

U.S. PATENT DOCUMENTS

2004/0077653 A1    4/2004 Xie et al. .............. 514/252.05

FOREIGN PATENT DOCUMENTS

WO    WO 02/076983    * 10/2002

OTHER PUBLICATIONS

Kittler et al., PubMed Abstract (Mol Neurobiol. 26(2–3):251–68), Oct.–Dec., 2002.*
Damasio, Alzheimer's Disease and Related Dementias, Cecil Textbook of Medicine, 20th Edition, vol. 2, pp. 1992–6, 1996.*
Drug Evaluations Annual 1991 (American Medical Association), pp. 202–210 and 262.

* cited by examiner

*Primary Examiner*—Deepak Rao
(74) *Attorney, Agent, or Firm*—Ann T. Kadlecek; Seth A. Fidel

(57) ABSTRACT

The invention provides 4-imidazol-1-ylmethyl pyrimidine of the formula

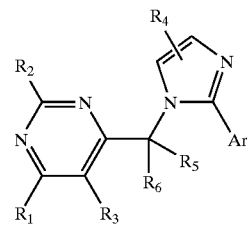

that bind to $GABA_A$ receptors. In the above formula, $R_1$, $R_2$, $R_3$, $R_4$, $R_5$, $R_6$ and Ar are defined herein. Such compounds may be used to modulate ligand binding to $GABA_A$ receptors in vivo or in vitro, and are particularly useful in the treatment of a variety of central nervous system (CNS) disorders in humans, domesticated companion animals, and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting $GABA_A$ receptors (e.g., receptor localization studies).

24 Claims, No Drawings

4-IMIDAZOL-1-YLMETHYL-PYRIMIDINE DERIVATIVES

CROSS-REFERENCE TO RELATED APPLICATIONS

This application claims priority to U.S. Provisional Application 60/424,945, filed Nov. 8, 2002.

FIELD OF THE INVENTION

The present invention relates generally to 4-imidazol-1-ylmethyl-pyrimidine derivatives that bind with high selectivity and/or high affinity to $GABA_A$ receptor. The present invention further relates to pharmaceutical compositions comprising such compounds and to the use of such compounds in the treatment of central nervous system (CNS) diseases.

BACKGROUND OF THE INVENTION

The $GABA_A$ receptor superfamily represents one of the classes of receptors through which the major inhibitory neurotransmitter γ-aminobutyric acid, or GABA, acts. Widely, although unequally, distributed throughout the mammalian brain, GABA mediates many of its actions through a complex of proteins called the $GABA_A$ receptor, which causes alteration in chloride conductance and membrane polarization. A number of drugs, including the anxiolytic and sedating benzodiazepines, also bind to this receptor. The $GABA_A$ receptor comprises a chloride channel that generally, but not invariably, opens in response to GABA, allowing chloride to enter the cell. This, in turn, effects a slowing of neuronal activity through hyperpolarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date, at least 6α, 3β, 3γ, 1ε, 1δ and 2ρ subunits have been identified. Native $GABA_A$ receptors are typically composed of 2 α subunits, 2 β subunits, and 1 γ subunit. Various lines of evidence (such as message distribution, genome localization and biochemical study results) suggest that the major naturally occurring receptor combinations are $α_1β_2γ_2$, $α_2β_3γ_2$, $α_3β_3γ_2$, and $α_5β_3γ_2$.

The $GABA_A$ receptor binding sites for GABA (2 per receptor complex) are formed by amino acids from the α and β subunits. Amino acids from the α and γ subunits together form one benzodiazepine site per receptor, at which benzodiazepines exert their pharmacological activity. In addition, the $GABA_A$ receptor contains sites of interaction for several other classes of drugs. These include a steroid binding site, a picrotoxin site, and a barbiturate site. The benzodiazepine site of the $GABA_A$ receptor is a distinct site on the receptor complex that does not overlap with the site of interaction for other classes of drugs or GABA.

In a classic allosteric mechanism, the binding of a drug to the benzodiazepine site alters the affinity of the GABA receptor for GABA. Benzodiazepines and related drugs that enhance the ability of GABA to open $GABA_A$ receptor channels are known as agonists or partial agonists, depending on the level of GABA enhancement. Other classes of drugs, such as β-carboline derivatives, that occupy the same site and negatively modulate the action of GABA are called inverse agonists. Those compounds that occupy the same site, and yet have little or no effect on GABA activity, can block the action of agonists or inverse agonists and are thus referred to as $GABA_A$ receptor antagonists.

The important allosteric modulatory effects of drugs acting at the benzodiazepine site were recognized early, and the distribution of activities at different receptor subtypes has been an area of intense pharmacological discovery. Agonists that act at the benzodiazepine site are known to exhibit anxiolytic, sedative, anticonvulsant and hypnotic effects, while compounds that act as inverse agonists at this site elicit anxiogenic, cognition enhancing, and proconvulsant effects.

While benzodiazepines have enjoyed long pharmaceutical use as anxiolytics, these compounds can exhibit a number of unwanted side effects such as cognitive impairment, sedation, ataxia, potentiation of ethanol effects, and a tendency for tolerance and drug dependence. Accordingly, there is a need in the art for additional therapeutic agents that modulate $GABA_A$ receptor activation and/or activity. The present invention fulfills this need, and provides further related advantages.

SUMMARY OF THE INVENTION

The present invention provides compounds that modulate $GABA_A$ receptor activation and/or $GABA_A$ receptor-mediated signal transduction. Such $GABA_A$ receptor modulators are preferably high affinity and/or high selectivity $GABA_A$ receptor ligands and act as agonists, inverse agonists or antagonists of $GABA_A$ receptors, such as human $GABA_A$ receptors. As such, they are useful in the treatment of various CNS disorders.

Within certain aspects, $GABA_A$ receptor modulators provided herein are 4-imidazol-1-ylmethyl-pyrimidine derivatives of Formula I:

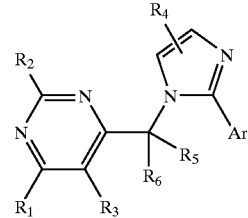

Formula I or a pharmaceutically acceptable form thereof, wherein:
$R_1$ is selected from:
  (a) hydrogen, halogen, nitro and cyano; and
  (b) groups of the formula:

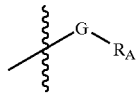

wherein:
    G is a bond, $C_1$–$C_8$alkyl, —N($R_B$)—, —O—, —C(=O)—, —C(=O)N($R_B$)—, —N($R_B$)C(=O)—, —S(O)$_m$—, —CH$_2$C(=O)—, —S(O)$_m$N($R_B$)— or —N($R_B$)S(O)$_m$—; wherein m is 0, 1 or 2; and
    $R_A$ and each $R_B$ are independently selected from:
      (a) hydrogen; and
      (b) $C_1$–$C_8$alkyl, $C_2$–$C_8$alkenyl, $C_2$–$C_8$alkynyl and 3- to 12-membered carbocycles and heterocycles, each of which is substituted with from 0 to 4 substituents independently selected from halogen, hydroxy, nitro, cyano, amino, $C_1$–$C_4$alkyl, $C_1$–$C_4$alkoxy, $C_1$–$C_4$alkanoyl, mono- and di($C_1$–$C_4$alkyl)amino, $C_1$–$C_4$haloalkyl and $C_1$–$C_4$haloalkoxy;

$R_2$ is hydrogen, halogen, hydroxy, nitro, cyano, amino, $C_1$–$C_4$alkyl, $C_1$–$C_4$haloalkyl, $C_1$–$C_4$alkoxy, $C_1$–$C_4$haloalkoxy, $C_3$–$C_7$cycloalkyl, or mono- or di-($C_1$–$C_4$alkyl)amino;

$R_3$ is hydrogen, halogen, hydroxy, nitro, cyano, amino, $C_1$–$C_8$alkyl, $C_2$–$C_8$alkenyl, $C_2$–$C_8$alkynyl, $C_3$–$C_7$cycloalkyl, $C_1$–$C_8$haloalkyl, $C_1$–$C_8$alkoxy, $C_1$–$C_8$haloalkoxy, $C_2$–$C_8$alkyl ether, $C_2$–$C_8$haloalkyl ether, or mono- or di-($C_1$–$C_8$alkyl)amino;

$R_4$ represents 0, 1 or 2 substituents independently chosen from halogen, hydroxy, nitro, cyano, amino, $C_1$–$C_4$alkyl, $C_1$–$C_4$alkoxy, mono- and di($C_1$–$C_4$alkyl)amino, $C_3$–$C_7$cycloalkyl, $C_1$–$C_2$haloalkyl and $C_1$–$C_2$haloalkoxy;

Ar represents phenyl, naphthyl or 5- to 10-membered heteroaryl, each of which is substituted with from 0 to 4 substituents independently selected from halogen, hydroxy, nitro, cyano, amino, $C_1$–$C_8$alkyl, $C_1$–$C_8$alkenyl, $C_1$–$C_8$alkynyl, $C_3$–$C_7$cycloalkyl ($C_0$–$C_8$alkyl), $C_1$–$C_8$haloalkyl, $C_1$–$C_8$alkoxy, $C_3$–$C_7$cycloalkyl($C_1$–$C_8$alkoxy), $C_1$–$C_8$haloalkoxy, $C_1$–$C_8$alkyl ether, $C_1$–$C_8$alkanone, $C_1$–$C_8$alkanoyl, 3- to 7-membered heterocycloalkyl($C_0$–$C_8$alkyl), oxo, $C_1$–$C_8$hydroxyalkyl, $C_1$–$C_8$aminoalkyl, and mono- and di-($C_1$–$C_8$alkyl)amino($C_0$–$C_8$alkyl); and $R_5$ and $R_6$ are independently hydrogen, halogen, methyl or ethyl.

Within further aspects, the present invention provides pharmaceutical compositions comprising one or more compounds or forms thereof as described above in combination with a pharmaceutically acceptable carrier, diluent or excipient. Packaged pharmaceutical preparations are also provided, comprising such a pharmaceutical composition in a container and instructions for using the composition to treat a patient suffering from a CNS disorder such as anxiety, depression, a sleep disorder, attention deficit disorder or Alzheimer's dementia.

The present invention further provides, within other aspects, methods for treating patients suffering from certain CNS disorders, such as anxiety, depression, a sleep disorder, attention deficit disorder, schizophrenia or Alzheimer's dementia, comprising administering to a patient in need of such treatment a $GABA_A$ receptor modulatory amount of a compound or form thereof as described above. Methods for improving short term memory in a patient are also provided, comprising administering to a patient in need of such treatment a $GABA_A$ receptor modulatory amount of a compound or form thereof as described above. Treatment of humans, domesticated companion animals (pets) or livestock animals suffering from certain CNS disorders with an effective amount of a compound of the invention is encompassed by the present invention.

In a separate aspect, the invention provides methods of potentiating the actions of other CNS active compounds. These methods comprise administering a $GABA_A$ receptor modulatory amount of a compound or salt of Formula I in conjunction with the administration of another CNS active compound.

The present invention relates to the use of compounds of Formula I as probes for the localization of $GABA_A$ receptors in sample (e.g., a tissue section). In certain embodiments, $GABA_A$ receptors are detected using autoradiography. Additionally, the present invention provides methods for determining the presence or absence of $GABA_A$ receptor in a sample, comprising the steps of: (a) contacting a sample with a compound as described above under conditions that permit binding of the compound to $GABA_A$ receptor; (b) removing compound that does not bind to the $GABA_A$ receptor and (c) detecting a level of compound bound to $GABA_A$ receptor.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

The present invention provides compounds that are 4-imidazol-1-ylmethyl-pyrimidine derivatives. Certain preferred compounds bind to $GABA_A$ receptor, preferably with high selectivity; more preferably such compounds further provide beneficial modulation of brain function. Without wishing to be bound to any particular theory of operation, it is believed that that interaction of such compounds with the benzodiazepine site of $GABA_A$ receptor results in the pharmacological effects of these compounds. Such compounds may be used in vitro or in vivo to determine the location of $GABA_A$ receptors or to modulate $GABA_A$ receptor activity in a variety of contexts.

Chemical Description and Terminology

Compounds provided herein are generally described using standard nomenclature. For compounds having asymmetric centers, it should be understood that (unless otherwise specified) all of the optical isomers and mixtures thereof are encompassed. All chiral (enantiomeric and diastereomeric), and racemic forms, as well as all geometric isomeric forms of a structure are intended, unless the specific stereochemistry or isomeric form is specifically indicated. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}C$, $^{13}C$, and $^{14}C$.

Certain compounds are described herein using a general formula that includes variables. Unless otherwise specified, each variable within such a formula is defined independently of other variables, and any variable that occurs more than one time within a formula is defined independently at each occurrence. Thus, for example, if a group is described as being substituted with 0–2 R*, then the group may be unsubstituted or substituted with up to two R* groups and R* at each occurrence is selected independently from the definition of R*. In addition, it will be apparent that combinations of substituents and/or variables are permissible only if such combinations result in stable compounds.

The phrase "4-imidazol-1-ylmethyl-pyrimidine derivative" as used herein, refers to compounds of Formula I, as well as pharmaceutically acceptable forms thereof.

"Pharmaceutically acceptable forms" of the compounds recited herein are pharmaceutically acceptable salts, hydrates, solvates, crystal forms, polymorphs, chelates, non-covalent complexes, esters, clathrates and prodrugs of such compounds. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

A "prodrug" is a compound that may not fully satisfy the structural requirements of Formula I, but is modified in vivo, following administration to a patient, to produce a compound of Formula I. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Prodrugs of the compounds of Formula I may be prepared, for example, by modifying functional groups present in the compounds in such a way that the modifications are cleaved in vivo to a compound of Formula I.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Optional substitution is also indicated by the phrase "substituted with from 0 to X substituents," in which X is the maximum number of substituents. Suitable substituents include, for example, halogen, cyano, amino, hydroxy, nitro, azido, carboxamido, —COOH, $SO_2NH_2$, alkyl (e.g., $C_1$–$C_8$alkyl), alkenyl (e.g., $C_2$–$C_8$alkenyl), alkynyl (e.g., $C_2$–$C_8$alkynyl), alkoxy (e.g., $C_1$–$C_8$alkoxy), alkyl ether (e.g., $C_2$–$C_8$alkyl ether), alkylthio (e.g., $C_1$–$C_8$alkylthio), haloalkyl (e.g., $C_1$–$C_8$haloalkyl), hydroxyalkyl (e.g., $C_1$–$C_8$hydroxyalkyl), aminoalkyl (e.g., $C_1$–$C_8$aminoalkyl), haloalkoxy (e.g., $C_1$–$C_8$haloalkoxy), alkanoyl (e.g., $C_1$–$C_8$alkanoyl), alkanone (e.g., $C_1$–$C_8$alkanone), alkanoyloxy (e.g., $C_1$–$C_8$alkanoyloxy), alkoxycarbonyl (e.g., $C_1$–$C_8$alkoxycarbonyl), mono- and di-($C_1$–$C_8$alkyl)amino, mono- and di-($C_1$–$C_8$alkyl) amino$C_1$–$C_8$alkyl, mono- and di-($C_1$–$C_8$alkyl)carboxamido, mono- and di-($C_1$–$C_8$alkyl)sulfonamido, alkylsulfinyl (e.g., $C_1$–$C_8$alkylsulfinyl), alkylsulfonyl (e.g., $C_1$–$C_8$alkylsulfonyl), aryl (e.g., phenyl), arylalkyl (e.g., ($C_6$–$C_{18}$aryl)$C_1$–$C_8$alkyl, such as benzyl and phenethyl), aryloxy (e.g., $C_6$–$C_{18}$aryloxy such as phenoxy), arylalkoxy (e.g., ($C_6$–$C_{18}$aryl)$C_1$–$C_8$alkoxy) and/or 3- to 8-membered heterocyclic groups such as coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino or pyrrolidinyl. Certain groups within the formulas provided herein are optionally substituted with from 1 to 2, 1 to 3 or 1 to 4 independently selected substituents.

A dash ("—") that is not between two letters or symbols is used to indicate a point of attachment for a substituent. For example, —CONH$_2$ is attached through the carbon atom.

As used herein, "alkyl" is intended to include both branched and straight-chain saturated aliphatic hydrocarbon groups, and where specified, having the indicated number of carbon atoms. Thus, the term $C_1$–$C_6$alkyl, as used herein, indicates an alkyl group having from 1 to 6 carbon atoms. "$C_0$–$C_4$alkyl" refers to a bond or a $C_1$–$C_4$alkyl group. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. In certain embodiments, preferred alkyl groups are methyl, ethyl, propyl, butyl, and 3-pentyl. "Aminoalkyl" is an alkyl group as defined herein substituted with one or more —NH$_2$ substituents. "Hydroxyalkyl" is a hydroxy group as defined herein substituted with one or more —OH substituents.

"Alkenyl" refers to a straight or branched hydrocarbon chain comprising one or more carbon-carbon double bonds, such as ethenyl and propenyl. Alkenyl groups include $C_2$–$C_8$alkenyl, $C_2$–$C_6$alkenyl and $C_2$–$C_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more carbon-carbon triple bonds. Alkynyl groups include $C_2$–$C_8$alkynyl, $C_2$–$C_6$alkynyl and $C_2$–$C_4$alkynyl groups, which have from 2 to 8, 2 to 6 or 2 to 4 carbon atoms, respectively. Alkynyl groups include for example groups such as ethynyl and propynyl.

By "alkoxy," as used herein, is meant an alkyl, alkenyl or alkynyl group as described above attached via an oxygen bridge. Alkoxy groups include $C_1$–$C_6$alkoxy and $C_1$–$C_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly "alkylthio" refers to an alkyl, alkenyl or alkynyl group as described above attached via a sulfur bridge.

A "cycloalkyl" is a saturated or partially saturated cyclic group in which all ring members are carbon, such as cyclopropyl, cyclobutyl, cyclopentyl, cyclohexyl, cycloheptyl, cyclooctyl, adamantyl, decahydronaphthalenyl, octahydro-indenyl, and partially saturated variants of any of the foregoing, such as cyclohexenyl. Such groups typically contain from 3 to about 10 ring carbon atoms; in certain embodiments, such groups have from 3 to 7 ring carbon atoms (i.e., $C_3$–$C_7$cycloalkyl). If substituted, any ring carbon atom may be bonded to any indicated substituent.

In the term "(cycloalkyl)alkyl", "cycloalkyl" and "alkyl" are as defined above, and the point of attachment is on the alkyl group. Certain such groups are $C_3$–$C_7$cycloalkyl ($C_0$–$C_8$alkyl), in which the cycloalkyl group is linked via a direct bond or a $C_1$–$C_8$alkyl. This term encompasses, for example, cyclopropylmethyl, cyclohexylmethyl and cyclohexylethyl. Similarly, "$C_3$–$C_7$cycloalkyl($C_1$–$C_8$alkoxy)" refers to a $C_3$–$C_7$cycloalkyl group linked via a $C_1$–$C_8$alkoxy.

The term "alkanoyl" refers to an alkyl group as defined above attached through a carbonyl bridge. Alkanoyl groups include $C_2$–$C_8$alkanoyl, $C_2$–$C_6$alkanoyl and $C_2$–$C_4$alkanoyl groups, which have from 2 to 8, 2 to 6 or 2 to 4 carbon atoms, respectively. "$C_1$-alkanoyl" refers to —(C=O)—H, which (along with $C_2$–$C_8$alkanoyl) is encompassed by the term "$C_1$–$C_8$alkanoyl." Ethanoyl is $C_2$alkanoyl.

The term "oxo," as used herein, refers to a keto (C=O) group. An oxo group that is a substituent of a nonaromatic ring results in a conversion of —CH$_2$— to —C(=O)—. It will be apparent that the introduction of an oxo substituent on an aromatic ring destroys the aromaticity.

An "alkanone" is an alkyl group as defined above with the indicated number of carbon atoms substituted at least one position with an oxo group. "$C_3$–$C_8$alkanone," "$C_3$–$C_6$alkanone" and "$C_3$–$C_4$alkanone" refer to an alkanone having from 3 to 8, 6 or 4 carbon atoms, respectively. By way of example, a $C_3$ alkanone group has the structure —CH$_2$—(C=O)—CH$_3$.

Similarly, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_4$alkyl ether groups, which have 2 to 8, 6 or 4 carbon atoms, respectively. By way of example, a $C_2$ alkyl ether group has the structure —CH$_2$—O—CH$_3$.

"Alkylamino" refers to a secondary or tertiary amine substituent having the general structure —NH-alkyl or —N(alkyl)(alkyl), wherein each alkyl may be the same or different. Such groups include, for example, mono- and di-($C_1$–$C_6$alkyl)amino groups, in which each alkyl may be the same or different and may contain from 1 to 6 carbon atoms, as well as mono- and di-($C_1$–$C_4$alkyl)amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-($C_1$–$C_4$alkyl) amino$C_0$–$C_4$alkyl, in which each alkyl may be the same or different, and in which the mono- or di-alkylamino group is linked via a direct bond or a $C_1$–$C_4$alkyl group. Examples of such group include methylaminomethyl and diethylaminomethyl.

The term "halogen" refers to fluorine, chlorine, bromine and iodine. A "haloalkyl" is a branched or straight-chain alkyl group, substituted with 1 or more halogen atoms (e.g., "$C_1$–$C_6$haloalkyl" groups have from 1 to 6 carbon atoms; "$C_1$–$C_4$haloalkyl" groups have from 1 to 4 carbon atoms). Examples of haloalkyl groups include, but are not limited to, mono-, di- or tri-fluoromethyl; mono-, di- or trichloromethyl; mono-, di-, tri-, tetra- or penta-fluoroethyl; and mono-, di-, tri-, tetra- or penta-chloroethyl. Typical haloalkyl groups are trifluoromethyl and difluoromethyl. The term "haloalkoxy" refers to a haloalkyl group as defined above attached via an oxygen bridge. "$C_1$–$C_6$haloalkoxy" groups have from 1 to 6 carbon atoms. The term "$C_2$–$C_8$haloalkyl ether" refers to a $C_2$–$C_8$alkyl ether group that is substituted with 1 or more halogens.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate, fused, spiro or pendant rings and from 6 to about 18 ring atoms, without heteroatoms as ring members. Representative aryl groups include phenyl, naphthyl, including 1-naphthyl and 2-naphthyl, and biphenyl. Bicyclic carbocyclic groups may, but need not comprise a cycloalkyl ring in addition to the aromatic ring (e.g., a tetrahydronapthyl group).

The term "carbocycle" or "carbocyclic group" is used herein to indicate saturated, partially unsaturated or aromatic groups having 1 ring or 2 fused, pendant or spiro rings, with 3 to 8 atoms in each ring, wherein all ring atoms are carbon. A carbocyclic group may be bound through any carbon atom that results in a stable structure, and may be substituted on any carbon atom if the resulting compound is stable. Carbocyclic groups include cycloalkyl and aryl groups.

A "heteroatom" as used herein is oxygen, sulfur or nitrogen.

The term "heterocycle" or "heterocyclic group" is used to indicate saturated, partially unsaturated, or aromatic groups having 1 or 2 rings, with 3 to 8 atoms in each ring, and in at least one ring from 1 to 4 independently chosen heteroatoms. The heterocyclic ring may be attached at any heteroatom or carbon atom that results in a stable structure, and may be substituted on carbon and/or nitrogen atom(s) if the resulting compound is stable. Any nitrogen and/or sulfur heteroatoms may optionally be oxidized, and any nitrogen may optionally be quaternized.

Certain heterocycles are "heteroaryl" (i.e., comprise at least one aromatic ring having from 1 to 4 heteroatoms), such as 5- to 7-membered monocyclic groups and 7- to 10-membered bicyclic groups. When the total number of S and 0 atoms in the heteroaryl group exceeds 1, then these heteroatoms are not adjacent to one another; preferably the total number of S and 0 atoms in the heteroaryl is not more than 1, 2 or 3, more preferably 1 or 2 and most preferably not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl and pyrazolyl. Bicyclic heteroaryl groups may, but need not, contain a saturated in addition to the aromatic ring (e.g., a tetrahydroquinolinyl or tetrahydroisoquinolinyl group). A "5- or 6-membered heteroaryl" is a monocyclic heteroaryl having 5 or 6 ring members.

Other heterocycles are referred to herein as "heterocycloalkyl" (i.e., saturated heterocycles). Heterocycloalkyl groups have from 3 to about 8 ring atoms, and more typically from 5 to 7 ring atoms. Examples of heterocycloalkyl groups include morpholinyl, piperazinyl and pyrrolidinyl. A 5- to 7-membered heterocycloalkyl($C_0$–$C_8$alkyl) group is a heterocycloalkyl group having from 5 to 7 ring members that is linked via a direct bond or a $C_1$–$C_8$alkyl group.

The terms "$GABA_A$ receptor" and "benzodiazepine receptor" refer to a protein complex that detectably binds GABA and mediates a dose dependent alteration in chloride conductance and membrane polarization. Receptors comprising naturally-occurring mammalian (especially human or rat) $GABA_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate $GABA_A$ receptor for GABA may be evaluated using a standard ligand binding assay as provided herein. It will be apparent that there are a variety of $GABA_A$ receptor subtypes that fall within the scope of the term "$GABA_A$ receptor." These subtypes include, but are not limited to, $\alpha_2\beta_3\gamma_2$, $\alpha_3\beta_3\gamma_2$, $\alpha_5\beta_3\gamma_2$, and $\alpha_1\beta_2\gamma_2$ receptor subtypes. $GABA_A$ receptors may be obtained from a variety of sources, such as from preparations of rat cortex or from cells expressing cloned human $GABA_A$ receptors. Particular subtypes may be readily prepared using standard techniques (e.g., by introducing mRNA encoded the desired subunits into a host cell, as described herein).

An "agonist" of a $GABA_A$ receptor is a compound that enhances the activity of GABA at the $GABA_A$ receptor. Agonists may, but need not, also enhance the binding of GABA to $GABA_A$ receptor. The ability of a compound to act as a $GABA_A$ agonist may be determined using an electrophysiological assay, such as the assay provided in Example 4.

An "inverse agonist" of a $GABA_A$ receptor is a compound that reduces the activity of GABA at the $GABA_A$ receptor. Inverse agonists, but need not, may also inhibit binding of GABA to the $GABA_A$ receptor. The reduction of GABA-induced $GABA_A$ receptor activity may be determined from an electrophysiological assay such as the assay of Example 4.

An "antagonist" of a $GABA_A$ receptor, as used herein, is a compound that occupies the benzodiazepine site of the $GABA_A$ receptor, but has no detectable effect on GABA activity at the $GABA_A$ receptor. Such compounds can inhibit the action of agonists or inverse agonists. $GABA_A$ receptor antagonist activity may be determined using a combination of a suitable $GABA_A$ receptor binding assay, such as the assay provided in Example 3, and a suitable functional assay, such as the electrophysiological assay provided in Example 4, herein.

A "$GABA_A$ receptor modulator" is any compound that acts as a $GABA_A$ receptor agonist, inverse agonist or antagonist. In certain embodiments, such a modulator may exhibit an affinity constant ($K_i$) of less than 1 micromolar in a standard $GABA_A$ receptor radioligand binding assay, or an $EC_{50}$ of less than 1 micromolar in an electrophysiological assay as provided in Example 4. In other embodiments a $GABA_A$ receptor modulator may exhibit an affinity constant or $EC_{50}$ of less than 500 nM, 200 nM, 100 nM, 50 nM, 25 nM, 10 nM or 5 nM.

A "$GABA_A$ receptor modulatory amount" is an amount of $GABA_A$ receptor modulator that, upon administration, results in an effective concentration of modulator at a target $GABA_A$ receptor. An effective concentration is a concentration that is sufficient to result in a statistically significant (i.e., $p \leq 0.05$, which is determined using a conventional parametric statistical analysis method such as a student's T-test) inhibition of total specific binding of $^3$H-Flumazenil within the assay described in Example 3.

A $GABA_A$ receptor modulator is said to have "high affinity" if the $K_i$ at a $GABA_A$ receptor is less than 1 micromolar, preferably less than 100 nanomolar or less than 10 nanomolar. A representative assay for determining $K_i$ at $GABA_A$ receptor is provided in Example 3, herein. It will be apparent that the $K_i$ may depend upon the receptor subtype used in the assay. In other words, a high affinity compound may be "subtype-specific" (i.e., the $K_i$ is at least 10-fold greater for one subtype than for another subtype). Such compounds are said to have high affinity for $GABA_A$ receptor if the $K_i$ for at least one $GABA_A$ receptor subtype meets the above criteria.

A $GABA_A$ receptor modulator is said to have "high selectivity" if it binds to a $GABA_A$ receptor with a $K_i$ that is at least 10-fold lower, preferably at least 100-fold lower, than the $K_i$ for binding to other membrane-bound receptors. In particular, the compound should have a $K_i$ that is at least 10-fold greater at the following receptors than at a $GABA_A$ receptor: serotonin, dopamine, galanin, VR1, C5a, MCH, NPY, CRF, bradykinin and tackykinin. Assays to determine $K_i$ at other receptors may be performed using standard binding assay protocols, such as using a commercially available membrane receptor binding assay (e.g., the binding assays available from MDS PHARMA SERVICES, Toronto, Canada and CEREP, Redmond, Wash.).

A "patient" is any individual treated with a compound provided herein. Patients include humans, as well as other animals such as companion animals and livestock. Patients may be afflicted with a CNS disorder, or may be free of such a condition (i.e., treatment may be prophylactic).

A "CNS disorder" is a disease or condition of the central nervous system that is responsive to $GABA_A$ receptor modulation in the patient. Such disorders include anxiety disorders (e.g., panic disorder, obsessive compulsive disorder, agoraphobia, social phobia, specific phobia, dysthymia, adjustment disorders, separation anxiety, cyclothymia, and generalized anxiety disorder), stress disorders (e.g., post-traumatic stress disorder, anticipatory anxiety acute stress disorder and acute stress disorder), depressive disorders (e.g., depression, atypical depression, bipolar disorder and depressed phase of bipolar disorder), sleep disorders (e.g., primary insomnia, circadian rhythm sleep disorder, dyssomnia NOS, parasomnias including nightmare disorder, sleep terror disorder, sleep disorders secondary to depression, anxiety and/or other mental disorders and substance-induced sleep disorder), cognitive disorders (e.g., cognition impairment, mild cognitive impairment (MCI), age-related cognitive decline (ARCD), schizophrenia, traumatic brain injury, Down's Syndrome, neurodegenerative diseases such as Alzheimer's disease and Parkinson's disease, and stroke), AIDS-associated dementia, dementia associated with depression, anxiety or psychosis, attention deficit disorders (e.g., attention deficit disorder and attention deficit and hyperactivity disorder), convulsive disorders (e.g., epilepsy), benzodiazepine overdose and drug and alcohol addiction.

A "CNS agent" is any drug used to treat or prevent a CNS disorder. CNS agents include, for example: serotonin receptor (e.g., 5-$HT_{1A}$) agonists and antagonists and selective serotonin reuptake inhibitors (SSRIs); neurokinin receptor antagonists; corticotropin releasing factor receptor ($CRF_1$)

antagonists; melatonin receptor agonists; nicotinic agonists; muscarinic agents; acetylcholinesterase inhibitors and dopamine receptor agonists.

Substituted 4-imidazol-1-ylmethyl-pyrimidine Derivatives

As noted above, the present invention provides compounds or Formula I, with the variables as described above, as well as pharmaceutically acceptable forms of such compounds. Within certain compounds of Formula I, $R_1$ is selected from: (a) hydrogen and halogen; and (b) groups of the formula:

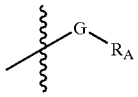

wherein: (i) G is a bond, —NH—, —N($R_B$)—, —O— or —C(=O)—; and (ii) $R_A$ and each $R_B$ are independently selected from $C_1$–$C_6$alkyl, $C_2$–$C_6$alkenyl, $C_2$–$C_6$alkynyl, piperidinyl, piperazinyl, morpholinyl, thienyl, pyridyl, pyrimidyl, pyrazolyl, thiazolyl and pyrazinyl, each of which is substituted with from 0 to 4 substituents independently selected from halogen, hydroxy, cyano, amino, $C_1$–$C_2$alkyl, and $C_1$–$C_2$alkoxy. For example, representative $R_1$ groups include (a) hydrogen and halogen; and (b) $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with hydroxy or $C_1$–$C_2$alkoxy.

$R_2$, within certain compounds of Formula I, is hydrogen or $C_1$–$C_4$alkyl. In some such compounds, $R_1$ is hydrogen, halogen, $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with hydroxy or $C_1$–$C_2$alkoxy.

$R_3$, within certain compounds of Formula I, is hydrogen, halogen, amino, $C_1$–$C_6$alkyl, $C_2$–$C_6$alkenyl, $C_2$–$C_6$alkynyl, $C_3$–$C_7$cycloalkyl, $C_1$–$C_6$haloalkyl, $C_1$–$C_6$alkoxy, $C_1$–$C_6$haloalkoxy or mono- or di-($C_1$–$C_6$alkyl)amino. Representative $R_3$ groups include, for example, hydrogen, $C_1$–$C_4$alkyl, $C_1$–$C_4$haloalkyl, $C_1$–$C_4$alkoxy and mono- and di-($C_1$–$C_4$alkyl)amino.

$R_4$, within certain compounds of Formula I, represents 0, 1 or 2 substituents independently chosen from halogen, hydroxy, methyl, ethyl, methoxy and trifluoromethyl. $R_4$ represents 0 substituents in some such compounds.

In certain compounds of Formula I, Ar represents phenyl or a 5- or 6-membered heteroaryl, each of which is substituted with from 0 to 4 substituents independently selected from halogen, hydroxy, nitro, cyano, amino, $C_1$–$C_6$alkyl, $C_1$–$C_6$alkenyl, $C_1$–$C_6$alkynyl, $C_1$–$C_6$haloalkyl, $C_1$–$C_6$alkoxy, $C_1$–$C_6$haloalkoxy, $C_3$–$C_7$cycloalkyl($C_0$–$C_6$alkyl), $C_3$–$C_7$cycloalkyl($C_1$–$C_6$alkoxy), 3- to 7-membered heterocycloalkyl($C_0$–$C_8$alkyl), $C_1$–$C_8$aminoalkyl, $C_1$–$C_6$hydroxyalkyl, and mono- and di-($C_1$–$C_6$alkyl)amino($C_0$–$C_6$alkyl). Representative Ar groups include, for example, phenyl, thiazolyl, pyrimidyl and pyridyl, each of which is substituted with from 0 to 4 substituents independently selected from halogen, hydroxy, cyano, amino, $C_1$–$C_4$alkyl, $C_1$–$C_4$alkenyl, $C_1$–$C_4$alkynyl, $C_1$–$C_4$haloalkyl, $C_1$–$C_4$alkoxy, $C_1$–$C_4$haloalkoxy and mono- and di-($C_1$–$C_4$alkyl)amino($C_0$–$C_4$alkyl); or each of which is substituted with from 0 to 3 substituents independently chosen from chloro, fluoro, cyano, amino, $C_1$–$C_4$alkyl, $C_1$–$C_4$alkoxy, $C_1$–$C_2$alkylamino, $C_1$–$C_2$haloalkyl and $C_1$–$C_2$haloalkoxy. In some such compounds, Ar represents phenyl or 2-pyridyl, each of which is substituted with 1, 2 or 3 substituents independently chosen from fluoro, chloro, cyano, trifluoromethyl and methyl.

Within certain compounds of Formula I, the variables carry the following definitions:

$R_1$ is:
(a) hydrogen or halogen; or
(b) $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with halogen, hydroxy or $C_1$–$C_2$alkoxy;

$R_2$ is hydrogen, halogen or $C_1$–$C_4$alkyl;

$R_3$ is hydrogen, $C_1$–$C_4$alkyl, $C_1$–$C_4$haloalkyl, $C_1$–$C_4$alkoxy, or mono- or di-($C_1$–$C_4$alkyl)amino;

$R_4$ represents 0, 1 or 2 substituents independently chosen from halogen, hydroxy, methyl, ethyl, methoxy and trifluoromethyl; and Ar represents phenyl, thiazolyl, or pyridyl, each of which is substituted with from 0 to 3 substituents independently chosen from chloro, fluoro, cyano, amino, $C_1$–$C_4$alkyl, $C_1$–$C_4$alkoxy, $C_1$–$C_2$alkylamino, $C_1$–$C_2$haloalkyl and $C_1$–$C_2$haloalkoxy.

Certain compounds of Formula I further satisfy Formula II:

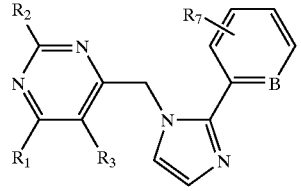

Formula II wherein:

B is CH or N;

$R_1$ is (a) hydrogen or halogen; or (b) $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with halogen, hydroxy or $C_1$–$C_2$alkoxy;

$R_2$ is hydrogen, halogen or methyl;

$R_3$ is hydrogen, $C_1$–$C_4$alkyl, $C_1$–$C_4$haloalkyl, $C_1$–$C_4$alkoxy, or mono- or di-($C_1$–$C_4$alkyl)amino; and $R_7$ represents from 0 to 3 substituents independently chosen from halogen, cyano, $C_1$–$C_4$alkyl, $C_1$–$C_4$alkoxy and $C_1$–$C_4$haloalkyl.

Within certain such compounds, $R_1$ is hydrogen, halogen, methyl or methoxy. In other such compounds, $R_1$ is pyridyl, pyrazolyl or thiazolyl.

Compounds provided herein detectably alter (modulate) ligand binding to GABA$_A$ receptor, as determined using a standard in vitro receptor binding assay. References herein to a "GABA$_A$ receptor ligand binding assay" are intended to refer to the standard in vitro receptor binding assay provided in Example 3. Briefly, a competition assay may be performed in which a GABA$_A$ receptor preparation is incubated with labeled (e.g., $^3$H) ligand, such as Flumazenil, and unlabeled test compound. Incubation with a compound that detectably modulates ligand binding to GABA$_A$ receptor will result in a decrease or increase in the amount of label bound to the GABA$_A$ receptor preparation, relative to the amount of label bound in the absence of the compound. Preferably, such a compound will exhibit a $K_i$ at GABA$_A$ receptor of less than 1 micromolar, more preferably less than 500 nM, 100 nM, 20 nM or 10 nM. The GABA$_A$ receptor used to determine in vitro binding may be obtained from a variety of sources, for example from preparations of rat cortex or from cells expressing cloned human GABA$_A$ receptors.

In certain embodiments, preferred compounds have favorable pharmacological properties, including oral bioavailability (such that a sub-lethal or preferably a pharmaceutically acceptable oral dose, preferably less than 2 grams, more preferably less than or equal to one gram or 200 mg, can provide a detectable in vivo effect), low toxicity (a preferred compound is nontoxic when a $GABA_A$ receptor-modulatory amount is administered to a subject), minimal side effects (a preferred compound produces side effects comparable to placebo when a $GABA_A$ receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1–27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120–27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a compound that "does not substantially inhibit cellular ATP production" is a compound that satisfies the criteria set forth in Example 5, herein. In other words, cells treated as described in Example 5 with 100 $\mu$M of such a compound exhibit ATP levels that are at least 50% of the ATP levels detected in untreated cells. In more highly preferred embodiments, such cells exhibit ATP levels that are at least 80% of the ATP levels detected in untreated cells.

A compound that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. In certain preferred embodiments, a dose of 0.01, 0.05. 0.1, 0.5, 1, 5, 10, 40 or 50 mg/kg administered parenterally or orally does not result in a statistically significant prolongation of heart QT intervals. By "statistically significant" is meant results varying from control at the $p<0.1$ level or more preferably at the $p<0.05$ level of significance as measured using a standard parametric assay of statistical significance such as a student's T test.

A compound "does not cause substantial liver enlargement" if daily treatment of laboratory rodents (e.g., mice or rats) for 5–10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternately, a compound "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the minimum therapeutically effective in vivo concentration.

Certain preferred compounds are not clastogenic or mutagenic (e.g., as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the minimum therapeutically effective in vivo concentration. In other embodiments, certain preferred compounds do not induce sister chromatid exchange (e.g., in Chinese hamster ovary cells) at such concentrations.

For detection purposes, as discussed in more detail below, compounds provided herein may be isotopically-labeled or radiolabeled. Such compounds are identical to those described above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, such as increased in vivo half-life or reduced dosage requirements and, hence, may be preferred in some circumstances.

As noted above, different stereoisomeric forms, such as racemates and optically active forms, are encompassed by the present invention. In certain embodiments, it may be desirable to obtain single enantiomers (i.e., optically active forms). Standard methods for preparing single enantiomers include asymmetric synthesis and resolution of the racemates. Resolution of the racemates can be accomplished by conventional methods such as crystallization in the presence of a resolving agent, or chromatography using, for example, a chiral HPLC column.

Pharmaceutical Compositions

The present invention also provides pharmaceutical compositions comprising at least one $GABA_A$ receptor modulator provided herein, together with at least one physiologically acceptable carrier or excipient. Such compounds may be used for treating patients in which $GABA_A$ receptor modulation is desirable (e.g., patients undergoing painful procedures who would benefit from the induction of amnesia, or those suffering from anxiety, depression, sleep disorders or cognitive impairment). Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs or cats). If desired, other active ingredients may also be included, such as additional CNS-active agents.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with one or more excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The compound, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of active compound release. The amount of compound contained within a sustained release formulation depends upon the site of implantation, the rate and expected duration of release and the nature of the condition to be treated or prevented.

Compounds provided herein are generally present within a pharmaceutical composition in a therapeutically effective amount. A therapeutically effective amount is an amount that results in a discernible patient benefit, such as diminution of symptoms of a CNS disorder. A preferred concentration is one sufficient to inhibit the binding of $GABA_A$ receptor ligand to $GABA_A$ receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating a CNS disorder such as anxiety, depression, a sleep disorder, attention deficit disorder or Alzheimer's dementia. Packaged pharmaceutical preparations include a container holding a therapeutically effective amount of at least one compound as described herein and instructions (e.g., labeling) indicating that the contained composition is to be used for treating the CNS disorder.

Methods of Use

Within certain aspects, the present invention provides methods for inhibiting the development of a CNS disorder. In other words, therapeutic methods provided herein may be used to treat an existing disorder, or may be used to prevent, decrease the severity of, or delay the onset of such a disorder in a patient who is free of detectable CNS disorder. CNS disorders are discussed in more detail below, and may be diagnosed and monitored using criteria that have been established in the art. Alternatively, or in addition, compounds provided herein may be administered to a patient to improve short-term memory. Patients include humans, domesticated companion animals (pets, such as dogs) and livestock animals, with dosages and treatment regimes as described above.

Frequency of dosage may vary, depending on the compound used and the particular disease to be treated or prevented. In general, for treatment of most disorders, a dosage regimen of 4 times daily or less is preferred. For the treatment of sleep disorders a single dose that rapidly reaches effective concentrations is desirable. Patients may generally be monitored for therapeutic effectiveness using assays suitable for the condition being treated or prevented, which will be familiar to those of ordinary skill in the art.

Within preferred embodiments, compounds provided herein are used to treat patients in need of such treatment. In general, such patients are treated with a $GABA_A$ receptor modulatory amount of a compound of Formula I (or a pharmaceutically acceptable form thereof), preferably the amount is sufficient to alter one or more symptoms of a CNS disorder. Compounds that act as agonists at $\alpha_2\beta_3\gamma_2$ and $\alpha_3\beta_3\gamma_2$ receptor subtypes are particularly useful in treating anxiety disorders such as panic disorder, obsessive compulsive disorder and generalized anxiety disorder; stress disorders including post-traumatic stress, and acute stress disorders. Compounds that act as agonists at $\alpha_2\beta_3\gamma_2$ and $\alpha_3\beta_3\gamma_2$ receptor subtypes are also useful in treating depressive or bipolar disorders, schizophrenia and sleep disorders, and may be used in the treatment of age-related cognitive decline and Alzheimer's disease. Compounds that act as inverse agonists at the $\alpha_5\beta_3\gamma_2$ receptor subtype or $\alpha_1\beta_2\gamma_2$ and $\alpha_5\beta_3\gamma_2$ receptor subtypes are particularly useful in treating cognitive disorders including those resulting from Down's Syndrome, neurodegenerative diseases such as Alzheimer's disease and Parkinson's disease, and stroke related dementia. Compounds that act as inverse agonists at the $\alpha_5\beta_3\gamma_2$ receptor subtype are particularly useful in treating cognitive disorders through the enhancement of memory, and particularly short-term memory, in memory-impaired patients; while those that act as agonists at the $\alpha_5\beta_3\gamma_2$ receptor subtype are particularly useful for the induction of amnesia. Compounds that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

CNS disorders that can be treated using compounds and compositions provided herein include:

Depression, e.g., depression, atypical depression, bipolar disorder, depressed phase of bipolar disorder.

Anxiety, e.g., general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g., sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g., cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety and psychosis (including schizophrenia and hallucinatory disorders).

Attention Deficit Disorder, e.g., attention deficit disorder (ADD), and attention deficit and hyperactivity disorder (ADHD).

Speech disorders, e.g., motor tic, clonic stuttering, dysfluency, speech blockage, dysarthria, Tourette's Syndrome and logospasm.

Compounds and compositions provided herein can also be used to improve short-term memory (working memory) in a patient. A therapeutically effective amount of a compound for improving short-term memory loss is an amount sufficient to result in a statistically significant improvement in any standard test of short-term memory function, including forward digit span and serial rote learning. For example, such a test may be designed to evaluate the ability of a patient to recall words or letters. Alternatively, a more complete neurophysical evaluation may be used to assess short-term memory function. Patients treated in order to improve short-term memory may, but need not, have been diagnosed with memory impairment or considered predisposed to development of such impairment.

In a separate aspect, the present invention provides methods for potentiating the action (or therapeutic effect) of other CNS agent(s). Such methods comprise administering a $GABA_A$ receptor modulatory amount of a compound provided herein in combination with another CNS agent. Such CNS agents include, but are not limited to the following: for anxiety, serotonin receptor (e.g., 5-$HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Within certain embodiments, the present invention provides a method of potentiating the antidepressant activity of selective serotonin reuptake inhibitors (SSRIs) by administering an effective amount of a GABA agonist compound provided herein in combination with an SSRI. An effective amount of compound is an amount sufficient to result in a detectable change in patient symptoms, when compared to a patient treated with the other CNS agent alone. Combination administration can be carried out using well known techniques (e.g., as described by Da-Rocha, et al. (1997) *J. Psychopharmacology* 11(3):211–218; Smith, et al. (1998) *Am. J. Psychiatry* 155(10):1339–45; and Le, et al. (1996) *Alcohol and Alcoholism* 31(suppl.):127–132. See also PCT International Publication Nos. WO 99/47142; WO 99/47171; WO 99/47131 and WO 99/37303.

The present invention also pertains to methods of inhibiting the binding of benzodiazepine compounds (i.e., compounds that comprise the benzodiazepine ring structure), such as RO15-1788 or GABA, to $GABA_A$ receptor. Such methods involve contacting a $GABA_A$ receptor modulatory amount of a compound provided herein with cells expressing $GABA_A$ receptor. This method includes, but is not limited to, inhibiting the binding of benzodiazepine compounds to $GABA_A$ receptors in vivo (e.g., in a patient given an amount of a $GABA_A$ receptor modulator provided herein that would be sufficient to inhibit the binding of benzodiazepine compounds or GABA to $GABA_A$ receptor in vitro). In one embodiment, such methods are useful in treating benzodiazepine drug overdose. The amount of $GABA_A$ receptor modulator that is sufficient to inhibit the binding of a benzodiazepine compound to $GABA_A$ receptor may be readily determined via a $GABA_A$ receptor binding assay as described in Example 3.

Within separate aspects, the present invention provides a variety of in vitro uses for the $GABA_A$ receptor modulators provided herein. For example, such compounds may be used as probes for the detection and localization of $GABA_A$ receptors, in samples such as tissue sections, as positive controls in assays for receptor activity, as standards and reagents for determining the ability of a candidate agent to bind to $GABA_A$ receptor, or as radiotracers for positron emission tomography (PET) imaging or for single photon emission computerized tomography (SPECT). Such assays can be used to characterize $GABA_A$ receptors in living subjects. Such compounds are also useful as standards and reagents in determining the ability of a potential pharmaceutical to bind to $GABA_A$ receptor.

Within methods for determining the presence or absence of $GABA_A$ receptor in a sample, a sample may be incubated with a $GABA_A$ receptor modulator as provided herein under conditions that permit binding of the $GABA_A$ receptor modulator to $GABA_A$ receptor. The amount of $GABA_A$ receptor modulator bound to $GABA_A$ receptor in the sample is then detected. For example, a $GABA_A$ receptor modulator may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method suitable for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of $GABA_A$ receptor in the sample. Detection assays, including receptor autoradiography (receptor mapping) of $GABA_A$ receptors in cultured cells or tissue samples may be performed as described by Kuhar in sections 8.1.1 to 8.1.9 of Current Protocols in Pharmacology (1998) John Wiley & Sons, New York.

For example, $GABA_A$ receptor modulators provided herein may be used for detecting $GABA_A$ receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of RO15-1788 to $GABA_A$ receptors within cell and tissue samples) at least one of the matched cell or tissue samples that has not previously been contacted with any $GABA_A$ receptor modulator provided herein with an experimental solution comprising a detectably-labeled preparation of the selected $GABA_A$ receptor modulator at the first measured molar concentration. The control sample is prepared in the same manner as the experimental sample and also contains an unlabelled preparation of the same compound at a greater molar concentration.

The experimental and control samples are then washed to remove unbound detectably-labeled compound. The amount of remaining bound detectably-labeled compound is then measured and the amount of detectably-labeled compound in the experimental and control samples is compared. The detection of a greater amount of detectable label in the washed experimental sample(s) than in control sample(s) demonstrates the presence of $GABA_A$ receptor in the experimental sample.

The detectably-labeled $GABA_A$ receptor modulator used in this procedure may be labeled with a radioactive label or a directly or indirectly luminescent label. When tissue sections are used in this procedure and the label is a radiolabel, the bound, labeled compound may be detected autoradiographically.

Compounds provided herein may also be used within a variety of well known cell culture and cell separation methods. For example, compounds may be linked to the interior surface of a tissue culture plate or other cell culture support, for use in immobilizing $GABA_A$ receptor-expressing cells for screens, assays and growth in culture. Such linkage may be performed by any suitable technique, such as the methods described above, as well as other standard techniques. Compounds may also be used to facilitate cell identification and sorting in vitro, permitting the selection of cells expressing a $GABA_A$ receptor. Preferably, the compound(s) for use in such methods are labeled as described herein. Within one preferred embodiment, a compound linked to a fluorescent marker, such as fluorescein, is contacted with the cells, which are then analyzed by fluorescence activated cell sorting (FACS).

Within other aspects, methods are provided for modulating binding of ligand to a $GABA_A$ receptor in vitro or in vivo, comprising contacting a $GABA_A$ receptor with a sufficient amount of a $GABA_A$ receptor modulator provided herein, under conditions suitable for binding of ligand to the receptor. The $GABA_A$ receptor may be present in solution, in a cultured or isolated cell preparation or within a patient. Preferably, the $GABA_A$ receptor is a present in the brain of a mammal. In general, the amount of compound contacted with the receptor should be sufficient to modulate ligand binding to $GABA_A$ receptor in vitro within, for example, a binding assay as described in Example 3.

Also provided herein are methods for altering the signal-transducing activity of cellular $GABA_A$ receptor (particularly the chloride ion conductance), by contacting $GABA_A$ receptor, either in vitro or in vivo, with a sufficient amount of a compound as described above, under conditions suitable for binding of Flumazenil to the receptor. The $GABA_A$ receptor may be present in solution, in a cultured or isolated cell or cell membrane preparation or within a patient, and the amount of compound may be an amount that would be sufficient to alter the signal-transducing activity of $GABA_A$ receptor in vitro. In certain embodiments, the amount of compound contacted with the receptor should be sufficient to modulate Flumazenil binding to $GABA_A$ receptor in vitro within, for example, a binding assay as described in Example 3. An effect on signal-transducing activity may be assessed as an alteration in the electrophysiology of the cells, using standard techniques. The amount of a compound that would be sufficient to alter the signal-transducing activity of $GABA_A$ receptors may be determined via a $GABA_A$ receptor signal transduction assay, such as the assay described in Example 4. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of $GABA_A$ receptors in cells in vitro may be determined from a detectable change in the electrophysiology of cells expressing $GABA_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be taken to indicate that a change in the electrophysiology of the animal's cells expressing GABA$_A$ receptors has occurred.

Preparation of Compounds

Compounds provided herein may generally be prepared using standard synthetic methods. Starting materials are generally readily available from commercial sources, such as Sigma-Aldrich Corp. (St. Louis, Mo.), or may be prepared as described herein. Representative procedures suitable for the preparation of compounds of Formula I are outlined in Schemes 1–5, herein, which are not to be construed as limiting the invention in scope or spirit to the specific reagents and conditions shown in them. Those having skill in the art will recognize that the reagents and conditions may be varied and additional steps employed to produce compounds encompassed by the present invention. In some cases, protection of reactive functionalities may be necessary to achieve the desired transformations. In general, such need for protecting groups, as well as the conditions necessary to attach and remove such groups, will be apparent to those skilled in the art of organic synthesis. Unless otherwise stated in the schemes below, the variables are as defined in Formula I.

Abbreviations used in Schemes 1–5 and the accompanying Examples are as follows:

Bu butyl
CDCl$_3$ deuterated chloroform
δ chemical shift
DCM dichloromethane
DME ethylene glycol dimethyl ether
DMF N,N-dimethylformamide
EtOAc ethyl acetate
ETOH ethanol
HOAc acetic acid
HPLC high pressure liquid chromatography
$^1$H NMR proton nuclear magnetic resonance
LC-MS liquid chromatography/mass spectrometry
MS mass spectrometry
(M+1) mass+1
Pd(PPh$_3$)$_4$ tetrakis(triphenylphosphine) palladium (0)
Pd$_2$(dba)$_3$ tris(dibenzylidineacetone) dipalladium (0)
THF tetrahydrofuran
TLC thin layer chromatography Scheme 1

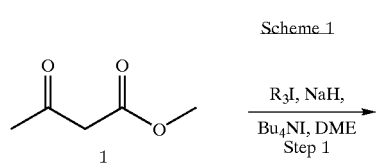

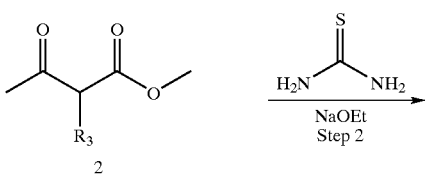

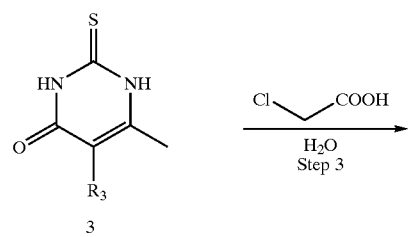

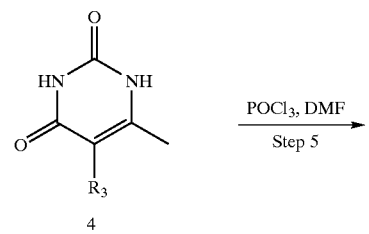

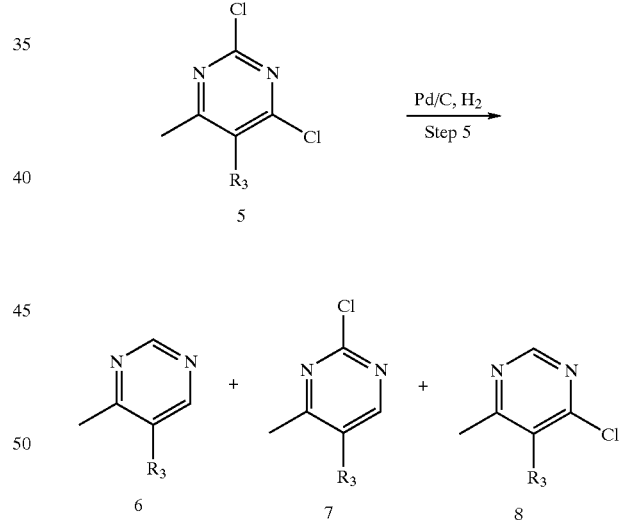

Scheme 2

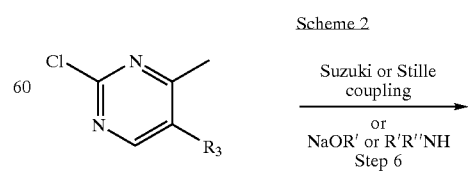

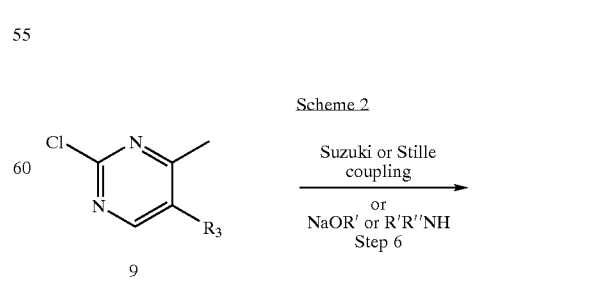

-continued

$R_1$ = alkyl, Ar, OR', NR'R''

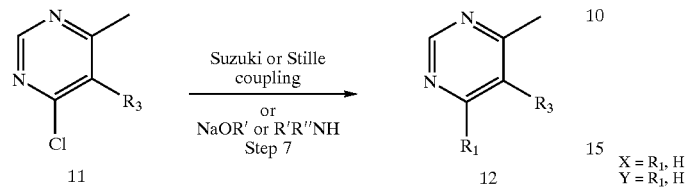

$R_1$ = alkyl, Ar, OR', NR'R''

Scheme 3

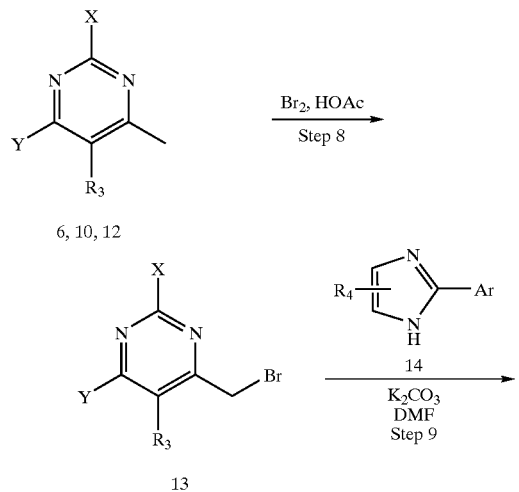

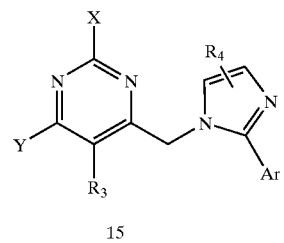

$X = R_1, H$
$Y = R_1, H$

Schemes 1, 2 and 3 illustrate the synthesis of a compound of Formula I (15). Alkylation of methyl acetoacetate 1 with an appropriate alkyl iodide gives 2 (Step 1), which reacts with thiourea in the presence of sodium ethoxide to afford 3 (Step 2). Conversion of 3 to 4 is achieved by refluxing 3 with chloroacetic acid (Step 3). Pyrimidine-2,4-dione 4 is treated with $POCl_3$ to give 2,4-dichloropyrimidine 5 (Step 4), which is hydrogenated in ethyl acetate in the presence of Pd/C to give a separable mixture of 6, 7 and 8 (Step 5). The chlorine atoms in 7 and 8 can be replaced by $R_1$ under either Suzuki/Stille coupling conditions with an appropriate boronic acid/tin reagent or nucleophilic substitution conditions with alkoxides/amines (Step 6 and 7). The methyl groups in 6, 10 and 12 can be selectively brominated to give 13 (Step 8), which is reacted with imidazole 14 (Step 9) to afford compounds of Formula I (15).

Scheme 4

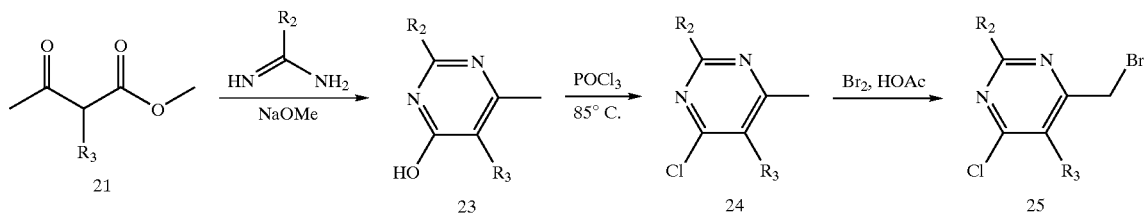

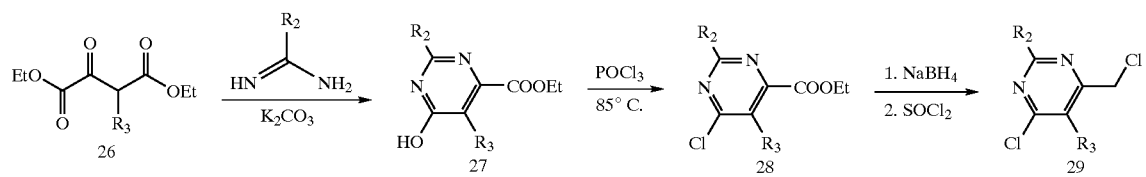

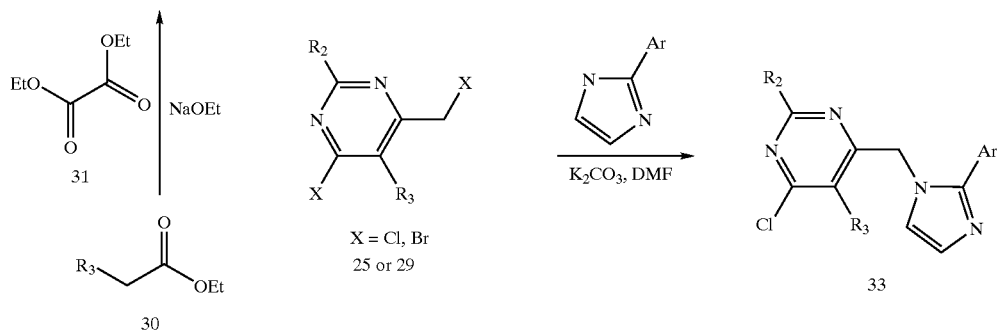

Scheme 4 illustrates the preparation of 6-chloro pyrimidine compounds 33 from bromomethyl or chloromethyl compounds 25 and 29. The condensation of ester 21 with amidine 22 is achieved by treatment with excess sodium methoxide in methanol. Treatment of 23 with $POCl_3$ gives the chloro-pyrimidine 24, which can be converted to bromomethyl pyrimidine 25 by bromination with $Br_2$ in HOAc at 85° C. Similarly, the condensation of ethyl ester 30 and diethyl oxalate 31 is easily effected by treatment with sodium ethoxide in ethanol. The resulting diester 26 is reacted with the corresponding amidine 22 and excess $K_2CO_3$ in refluxing ethanol, to provide pyrimidinone 27. The transformation of 27 to the 6-chloro-pyrimidine ester 28 is effected by treatment with $POCl_3$ at 85° C. Compound 28 is then converted to chloromethyl pyrimidine 29 by $NaBH_4$ reduction followed by thionyl chloride treatment. The bromide 25 or chloride 29 is then reacted with imidazole 14 in DMF in the presence of excess $K_2CO_3$ to afford compound 33.

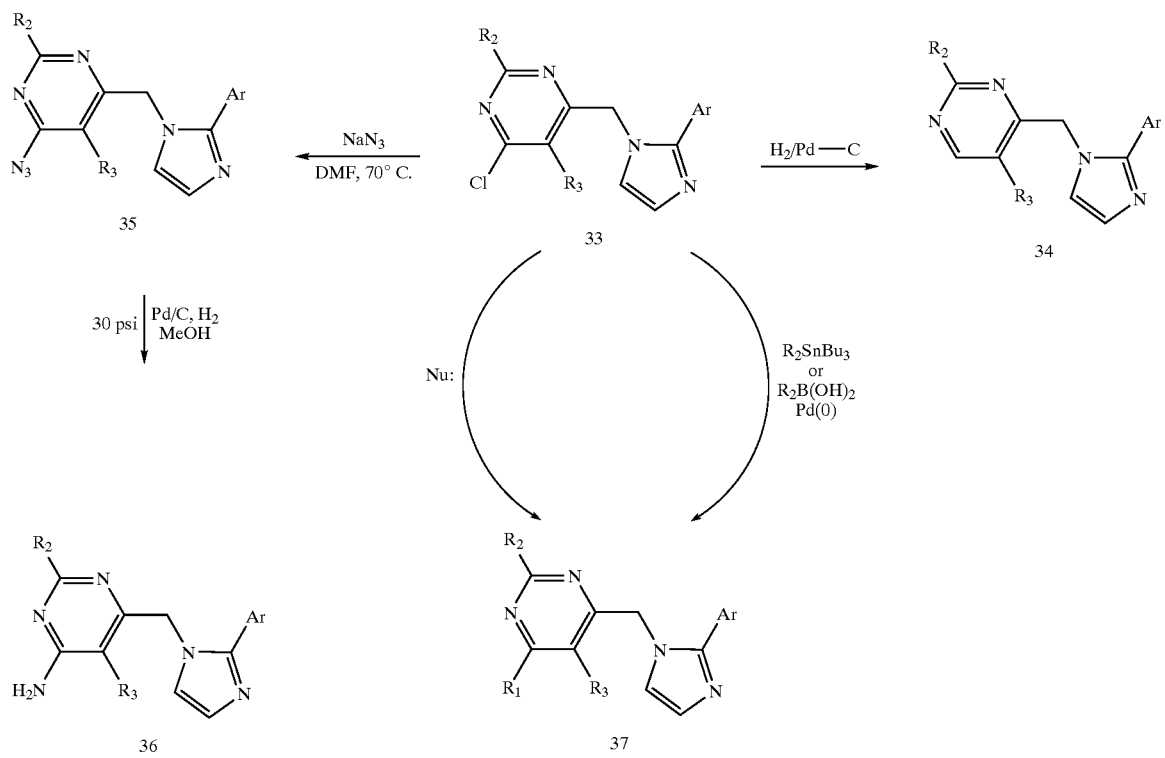

Scheme 5 illustrates the conversion of compounds 33 to compounds 34, 35 and 36. Reduction of 33 with $H_2$ under Pd-C catalytic conditions provides compounds 34. Aminopyrimidines 36 are prepared from 33 by azide displacement, followed by $H_2$ reduction. Compounds 33 are converted to compounds 37 by Suzuki or Stille coupling, or by other nucleophilic substitutions.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

The following Examples are offered by way of illustration and not by way of limitation. Unless otherwise specified, all reagents and solvents are of standard commercial grade and are used without further purification. Starting materials and intermediates described herein may generally be obtained from commercial sources, prepared from commercially available organic compounds or prepared using well known synthetic methods.

EXAMPLES

Starting materials and various intermediates described in the following Examples may be obtained from commercial sources, prepared from commercially available organic compounds, or prepared using known synthetic methods. Representative examples of methods suitable for preparing intermediates of the invention are also set forth below.

In the following Examples, LC-MS conditions for the characterization of the compounds herein are:

1. Analytical HPLC-MS instrumentation: Analyses are performed using a Waters 600 series pump (Waters Corporation, Milford, Mass.), a Waters 996 Diode Array Detector and a Gilson 215 auto-sampler (Gilson Inc, Middleton, Wis.), Micromass® LCT time-of-flight electrospray ionization mass analyzer. Data are acquired using MassLynx™ 4.0 software, with OpenLynx Global Server™, OpenLynx™, and AutoLynx™ processing.
2. Analytical HPLC conditions: 4.6×50 mm, Chromolith™ SpeedROD RP-18e column (Merck KGaA, Darmstadt, Germany); UV 10 spectra/sec, 220–340 nm summed; flow rate 6.0 mL/min; injection volume 1 µl; Gradient conditions—mobile phase A is 95% water, 5% methanol with 0.05% TFA; mobile phase B is 95% methanol, 5% water with 0.025% TFA, and the gradient is 0–0.5 minutes 10–100% B, hold at 100% B to 1.2 minutes, return to 10% B at 1.21 minutes inject-to-inject cycle time is 2.15 minutes.
3. Analytical MS conditions: capillary voltage 3.5 kV; cone voltage 30V; desolvation and source temperature are 350° C. and 120° C., respectively; mass range 181–750 with a scan time of 0.22 seconds and an inter scan delay of 0.05 minutes.

Example 1

Synthesis of Representative Substituted 4-(2-arylimidazol-1-ylmethyl)pyrimidines 1. Preparation of 2-acetyl-pentanoic Acid Methyl Ester

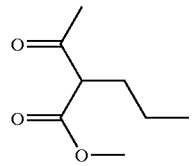

A solution of methyl acetoacetate (10.8 mL, 100 mmol) in DME (50 mL) is added dropwise to a suspension of NaH (95% dry, 2.44 g, 100 mmol) in DME (250 mL) cooled to 0° C. The resulting solution is stirred at room temperature for 1 hour. Bu₄NI (3.7 g, 10 mmol) is added, followed by PrI. The mixture is then stirred at reflux for 6 hours. The solvent is removed in vacuo and water (200 mL) and EtOAc (200 mL) are added. The layers are separated and the aqueous layer is extracted with EtOAc (200 mL). The combined extracts are washed with brine (200 mL) and dried (Na₂SO₄). Evaporation of the solvent provides a light yellow oil. Flash column chromatography of the residue by silica gel, eluting with 7:1 hexane, EtOAc provides the title product as a colorless oil. LC-MS, M+1 159.2

2. Preparation of 6-methyl-5-propyl-2-thio-2,3-dihydropyrimidin-4-one

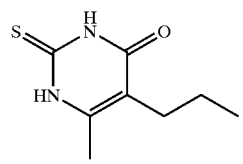

A mixture of 2-acetyl-pentanoic acid methyl ester (3.0 g, 19 mmol), thiourea (7.23 g, 95 mmol) and NaOEt (7.76 g, 114 mmol) in EtOH (50 mL) is stirred at reflux for 4 hours. Solvent is removed in vacuo and the residue is dissolved in water (40 mL). The solution is carefully acidified to pH 4 with concentrated HCl and the mixture is stirred at 0° C. for 45 minutes. The solid formed is filtered and washed with water and then dried to provide the title compound as a light yellow solid. LC-MS, M+1 185.1

3. Preparation of 6-methyl-5-propyl-pyrimidin-2,4-dione

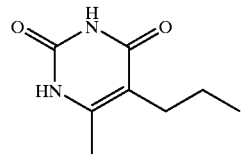

A 10% aqueous solution of chloroacetic acid (40 mL) is added to 6-methyl-5-propyl-2-thio-2,3-dihydropyrimidin-4-one (1.74 g, 9.4 mmol). The mixture is heated at reflux for 4 hours and then cooled in an ice bath. The solid which forms is collected by filtration and washed with water and dried, to provide a white solid. LC-MS, M+1 169.2

4. Preparation of 2,4-dichloro-6-methyl-5-propyl-pyrimidine

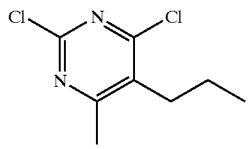

A mixture of 6-methyl-5-propyl-pyrimidin-2,4-dione (1.68 g, 10 mmol) and POCl$_3$ (10 mL) and DMF (3 drops) is stirred at 85° C. for 4 hours. The solvent is removed in vacuo and EtOAc (20 mL) and water (20 mL) are added to the residue. The layers are separated and the aqueous layer extracted with EtOAc (20 mL). The combined extracts are washed with brine (20 mL) and dried (Na$_2$SO$_4$). Evaporation of the solvent provides a light yellow oil, which is used for next step without further purification. LC-MS, M+1 206.2

5. Hydrogenation of 2,4-dichloro-6-methyl-5-propyl-pyrimidine

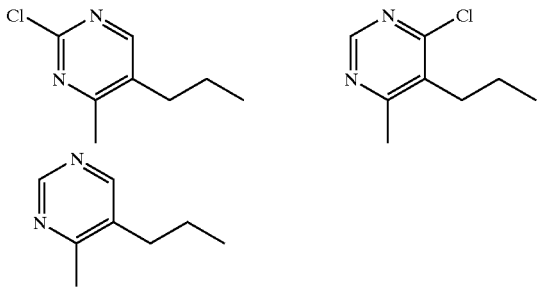

5% Pd/C (25 mg) and CH$_3$COONa (820 mg, 10 mmol) are added to a solution of 2,4-dichloro-6-methyl-5-propyl-pyrimidine (1.02 g, 5 mmol) in EtOAc (25 mL). The mixture is hydrogenated at 50 psi overnight. The catalyst is filtered and the solvent removed in vacuo. Flash column chromatography of the residue on silica gel by 4:1 hexane:EtOAc provides 2-chloro-6-methyl-5-propyl-pyrimidine (LC-MS, M+1 171.7), 4-chloro-6-methyl-5-propyl-pyrimidine (LC-MS, M+1 171.7) and 6-methyl-5-propyl-pyrimidine (LC-MS, M+1 157.7) as a 1:1:1.5 mixture.

6. Preparation of 2-alkoxy/N,N-dialkylamino or 4-alkoxy/N,N-dialkylamino-6-methyl-5-propyl-pyrimidine A. 2-alkoxy- or 4-alkoxy-6-methyl-5-propyl-pyrimidine Sodium alkoxide (4 mmol) is added to a stirred solution of 2-chloro or 4-chloro-6-methyl-5-propyl-pyrimidine (340 mg, 2 mmol) in THF (10 mL). The reaction mixture is stirred at reflux overnight and then poured into 1N HCl (5 mL). The resulting solution is then neutralized by saturated NaHCO$_3$. EtOAc (15 mL) is added and the layers are separated. The aqueous layer is extracted with EtOAc (10 mL) and the combined extracts are washed with brine (10 mL), dried (Na$_2$SO$_4$) and evaporated. The residue is purified by flash column chromatography, which gives 2-alkoxy- or 4-alkoxy-6-methyl-5-propyl-pyrimidine as light yellow oils.

B. 2-(N,N-dialkylamino) or 4-(N,N-dialkylamino)-6-methyl-5-propyl-pyrimidine 2-chloro or 4-chloro-6-methyl-5-propyl-pyrimidine (340 mg, 2 mmol) and a secondary amine (8 mL) are heated at 120° C. overnight in sealed tube. Solvent is removed in vacuo. Flash column separation of the residue provides the N,N-dialkylamino compounds.

7. Preparation of 2-aryl/alkyl or 4-aryl/alkyl 6-methyl-5-propyl-pyrimidine

A. Suzuki Approach

A mixture of 2-chloro or 4-chloro-6-methyl-5-propyl-pyrimidine (340 mg, 2 mmol) aryl or alkyl boronic acid (3 mmol), Pd$_2$(dba)$_3$ (56 mg, 0.06 mmol), (t-Bu)$_3$P (12 mg, 0.06 mmol) and Cs$_2$CO$_3$ (978 mg, 3 mmol) in dioxane (10 mL) is degassed. The mixture is then heated at 100° C. for 6 hours. The solvent is removed in vacuo and water (10 mL) and EtOAc (15 mL) is added. The layers are separated and the aqueous layer extracted with EtOAc (15 mL). The combined extracts are washed with brine (20 mL), dried (Na$_2$SO$_4$), and evaporated. Preparative TLC purification of the residue provides the title products.

B. Stille Approach

A mixture of 2-chloro or 4-chloro-6-methyl-5-propyl-pyrimidine (340 mg, 2 mmol), alkyl or aryltributyl tin (3 mmol), Pd(PPh$_3$)$_4$ (0.06 mmol, 68 mg) in toluene (10 mL) is degassed. The mixture is then heated at 100° C. overnight. Saturated KF aqueous solution (8 mL) is added and the mixture is stirred for 15 minutes. The layers are separated and the aqueous layer is extracted with EtOAc (10 mL). The combined extracts are washed with brine (15 mL), dried (Na$_2$SO$_4$), and evaporated. Preparative TLC purification of the residue provides the title products.

8. Preparation of Substituted 6-bromomethyl-5-propyl-pyrimidine

Bromine (0.153 mL, 3 mmol) is added dropwise to a solution of 6-methyl-5-propyl-pyrimidine (3 mmol) in HOAc (10 mL) heated at 85° C. After the addition, the mixture is stirred at 85° C. for 1 hour. The solvent is removed in vacuo, the residue dissolved in EtOAc (15 mL), and washed with Na$_2$S$_2$O$_3$ solution (saturated 5 mL) followed by NaHCO$_3$ (10 mL) and brine (10 mL). The organic phase is dried (Na$_2$SO$_4$) and evaporated. The resulting yellow oil is purified by flash column chromatography to provide the title compound.

9. Preparation of Substituted 4-(2-aryl-imidazol-1-ylmethyl) pyrimidines

Excess K$_2$CO$_3$ is added to a stirred solution of substituted 6-bromomethyl-5-propyl-pyrimidine (0.32 mmol) and 2-aryl-1H-imidazole (0.32 mmol) in DMF (6 mL). The mixture is stirred at room temperature overnight. The solvent is removed in vacuo and water (5 mL) and EtOAc (8 mL) are added. The layers are separated and the aqueous layer is extracted with EtOAc (8 mL). The combined extracts are washed with brine (10 mL), dried (Na$_2$SO$_4$), and evaporated. Preparative TLC purification of the residue (5% MeOH in CH$_2$Cl$_2$) provides the substituted 4-(2-aryl-imidazol-1-ylmethyl)pyrimidine.

Example 2

Synthesis of Representative Substituted 4-imidazol-1-ylmethyl-pyrimidine Derivatives This Example illustrates the synthesis of certain representative substituted 4-imidasol-1-ylmethyl-pyrimidine derivatives. Within the following synthetic methods, certain starting materials are 2-arylimidazoles. Such compounds are generally prepared as follows. Glyoxal (40% w/w H$_2$O, 16.0 g, 0.110 mol) and ammonium hydroxide (con. 29 mL) are added to a solution of the corresponding ArCHO (0.092 mol) in methanol (450 mL) at 0° C. The mixture is allowed to warm gradually to room temperature over an 18 hour period. The solvent is removed. Water (100 mL) is added to the residue and the mixture is extracted with methylene chloride (5×150 mL). The combined organic layers are washed with brine (2×100 mL), dried, and solvent removed. The crude product is separated by column chromatography (5% MeOH in DCM) to give the 2-arylimidazole as a solid.

Compound 1

4-Chloro-6-[2-(6-fluoro-pyridin-2-yl)-imidazol-1-ylmethyl]-2-methyl-5-propyl-pyrimidine

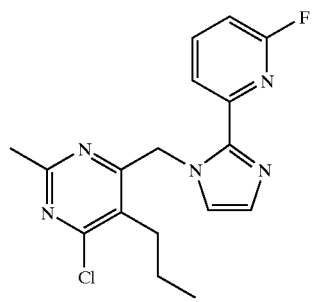

Step 1. Preparation of 2-Oxo-3-propyl-succinic Acid Diethyl Ester

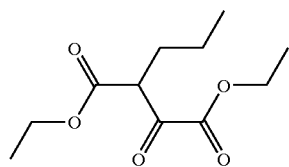

At room temperature, a mixture of pentanoic acid ethyl ester (0.4 mol) and diethyl oxalate (73.1 g, 0.5 mol) is added to a solution of NaOEt (32.7 g, 0.48 mol) in EtOH (250 mL). The mixture is stirred at room temperature for 30 minutes. Then a simple distillation apparatus is set up and ethanol is distilled away. The residue is then purified by vacuum distillation, which provides the title compound as a clear oil.

Step 2. Preparation of 2-Methyl-5-propyl-6-hydroxy-pyrimidine-4-carboxylic Acid Ethyl Ester

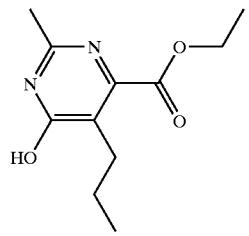

A mixture of 2-oxo-3-propyl-succinic acid diethyl ester (20 mmol), acetamidine hydrochloride (40 mmol), and $K_2CO_3$ (6.9 g, 50 mmol) in ethanol (50 mL) is heated at 70° C. overnight. The solid is filtered and the residue is dissolved in water (30 mL). Acetic acid is added to adjust the pH=4. The mixture is then extracted with $CH_2Cl_2$ (4×50 mL) and the combined extracts are washed with brine (100 mL). The solution is dried ($Na_2SO_4$) and evaporated in vacuo to give a light yellow solid. The solid is used without further purification in the next step.

Step 3. Preparation of 2-Methyl-5-propyl-6-chloro-pyrimidine-4-carboxylic Acid Ethyl Ester

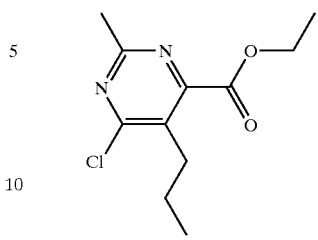

A mixture of 2-methyl-5-propyl-6-hydroxy-pyrimidine-4-carboxylic acid ethyl ester (10 mmol) and $POCl_3$ (25 mL) is heated at 85° C. for 4 hours. The solvent is removed in vacuo and EtOAc (40 mL) and water (30 mL) are added to the residue. $NaHCO_3$ is carefully added until the pH of aqueous layer is greater than 7. The layers are separated and the aqueous layer is extracted with EtOAc (2×30 mL). The combined extracts are washed with brine (50 mL), dried ($Na_2SO_4$), and evaporated. Flash column purification of the residue with 3:1 EtOAc, hexane provides 2-methyl-5-propyl-6-chloro-pyrimidine-4-carboxylic acid ethyl ester as a light yellow oil.

Step 4. Preparation of 2-Methyl-5-propyl-4-chloromethyl-6-chloro-pyrimidine

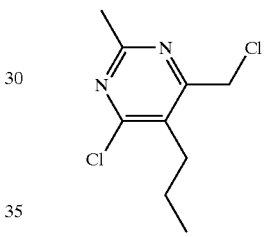

$NaBH_4$ (91 mg, 2.4 mmol) is added to a solution of 2-methyl-5-propyl-6-chloro-pyrimidine-4-carboxylic acid ethyl ester (0.48 mmol) in MeOH (10 mL) cooled to 0° C. and the mixture is stirred at room temperature overnight. The solvent is removed in vacuo and water (10 mL) and EtOAc (10 mL) are added to the residue. The layers are separated and the aqueous layer is extracted with EtOAc (10 mL). The combined extracts are washed with brine (20 mL), dried ($Na_2SO_4$), and evaporated. The resulting light oil is then dissolved in $CH_2Cl_2$ (5 mL) and thionyl chloride (1 mL) is added to it. The mixture is stirred at room temperature for 4 hours. The solvent is then removed. EtOAc (15 mL) is added to the residue and it is washed with $NaHCO_3$ (15 mL) and brine (15 mL), then dried ($Na_2SO_4$), and evaporated. Flash column chromatography of the residue provides the title compound as a yellowish oil.

Step 5. Preparation of 4-Chloro-6-[2-(6-fluoro-pyridin-2-yl)-imidazol-1-ylmethyl]-2-methyl-5-propyl-pyrimidine

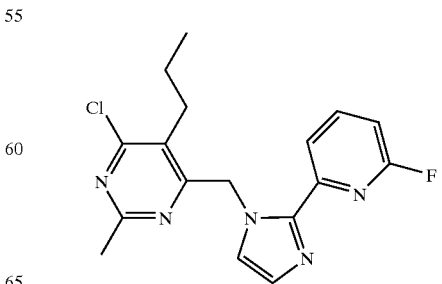

A mixture of 2-methyl-5-propyl-4-chloromethyl-6-chloro-pyrimidine (1 mmol), 6-fluoro-2-(1H-imidazol-2-yl)-pyridine (163 mg, 1 mmol), and K$_2$CO$_3$ (552 mg, 4 mmol) in DMF (6 mL) is stirred at room temperature overnight. The solvent is removed in vacuo and EtOAc (10 mL) and water (10 mL) are added to the residue. The layers are separated and the aqueous layer is extracted with EtOAc (10 mL). The combined extracts are washed with brine (10 mL), dried (Na$_2$SO$_4$), and evaporated. Preparative TLC separation of the residue with 5% MeOH in CH$_2$Cl$_2$ provides the title compound as a white solid. $^1$H-NMR (CDCl$_3$) δ: 8.13 (dd, 1H), 7.82 (t, 1H), 7.19 (d, 1H), 7.09 (d, 1H), 6.79 (dd, 1H), 5.98 (s, 2H), 2.79–2.84 (m, 2H), 2.49 (s, 3H), 1.53–1.61 (m, 2H), 0.98 (t, 3H).

Compound 2
4-Chloro-6-[2-(3-fluoro-pyridin-2-yl)-imidazol-1-ylmethyl]-2-methyl-5-propyl-pyrimidine

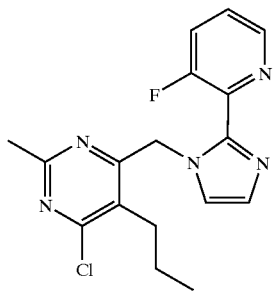

This compound is prepared using a procedure similar to that described for Compound 1. $^1$H-NMR (CDCl$_3$) δ: 8.27–8.29 (m, 1H), 7.49–7.55 (m, 1H), 7.22–7.28 (m, 2H), 7.09 (d, 1H), 5.77 (s, 2H), 2.64–2.69 (m, 2H), 2.48 (s, 3H), 1.44–1.52 (m, 2H), 0.94 (s, 3H).

Compound 3
4-Chloro-6-[2-(3-fluoro-pyridin-2-yl)-imidazol-1-ylmethyl]-5-propyl-pyrimidine

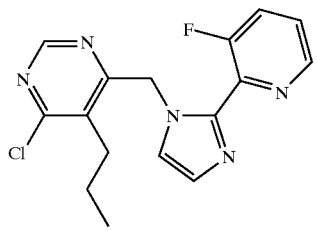

Step 1. Preparation of 5-Propyl-6-methyl-pyrimidin-4-one

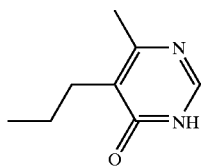

NaOMe (1.30 g, 24 mmol) is added to a stirred solution of formamidine (12 mmol) in MeOH (75 mL) at room temperature. The mixture is stirred for 15 minutes. 2-Acetylpentanoic acid methyl ester (10 mmol) is added and the mixture is stirred at room temperature overnight. Acetic acid (0.72 g, 12 mmol) is added and the solvent is removed in vacuo. Water (30 mL) is added to the residue and it is extracted with 2-butanone (3×30 mL). The combined extracts are washed with brine (40 mL), dried (Na$_2$SO$_4$), and evaporated, to provide a yellow solid. This solid is used in the next step without further purification.

Step 2. Preparation of 5-Propyl-4-chloro-6-methyl-pyrimidine

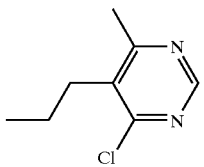

A mixture of 5-propyl-6-methyl-pyrimidin-4-one (10 mmol) and POCl$_3$ (25 mL) is heated at 85° C. for 4 hours. The solvent is removed in vacuo and EtOAc (30 mL) and water (30 mL) are added to the residue. NaHCO$_3$ is carefully added until the pH of aqueous layer is greater than 7. The layers are separated and the aqueous layer is extracted with EtOAc (2×30 mL). The combined extracts are washed with brine (50 mL), dried (Na$_2$SO$_4$), and evaporated. Flash column purification of the residue with 6:1 EtOAc, hexane provides the title product as a light yellow oil.

Step 3. Preparation of 5-Propyl-6-bromomethyl-4-chloro-pyrimidine

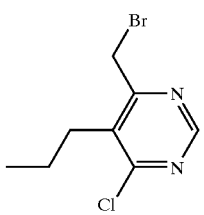

Br$_2$ (1.28 g, 8 mmol) is added dropwise to a stirred solution of 5-propyl-4-chloro-6-methyl-pyrimidine (8 mmol) in HOAc (20 mL) heated at 85° C. After addition, the mixture is stirred at 85° C. for 1 hour. The solvent is removed in vacuo and EtOAc (25 mL) and NaHCO$_3$ (25 mL) are added to the residue. The layers are separated and the organic layer is washed with Na$_2$S$_2$O$_3$ solution (sat. 15 mL) followed by brine (20 mL). The organic phase is dried (Na$_2$SO$_4$) and evaporated. The resulting yellow oil is purified by flash column (6:1 EtOAc:hexane) to afford the title product as a light yellow solid.

Step 4. Preparation of 4-Chloro-6-[2-(3-fluoro-pyridin-2-yl)-imidazol-1-ylmethyl]-5-propyl-pyrimidine

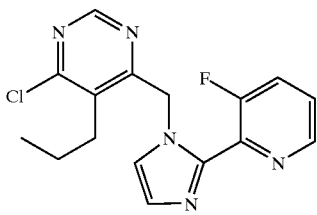

A mixture of 5-propyl-6-bromomethyl-4-chloro-pyrimidine (1 mmol), 3-fluoro-2-(1H-imidazol-2-yl)-pyridine (163 mg, 1 mmol), and K$_2$CO$_3$ (552 mg, 4 mmol) in DMF (6 mL) is stirred at room temperature overnight. The solvent is removed in vacuo and EtOAc (10 mL) and water (10 mL) are added to the residue. The layers are separated and the aqueous layer is extracted with EtOAc (10 mL). The combined extracts are washed with brine (10 mL), dried (Na$_2$SO$_4$), and evaporated. Preparative TLC separation of the residue with 5% MeOH in CH$_2$Cl$_2$ provides the title compound as a white solid. $^1$H-NMR (CDCl$_3$) δ: 8.65 (S, 1H), 8.24 (d, 1H), 7.53 (t, 1H), 7.32 (s, 1H), 7.27–7.22 (m, 1H), 7.12 (s, 1H), 5.87 (s, 2H), 2.76 (t, 2H), 1.68–1.54 (m, 2H), 1.01 (t, 3H).

Compound 4

4-[2-(3-Fluoro-pyridin-2-yl)-imidazol-1-ylmethyl]-2-methyl-5-propyl-pyrimidine

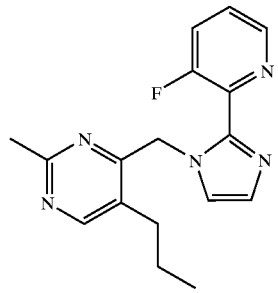

A mixture of 4-chloro-6-[2-(3-fluoro-pyridin-2-yl)-imidazol-1-ylmethyl]-2-methyl-5-propyl-pyrimidine (55.3 mg, 0.16 mmol), K$_2$CO$_3$ (30 mg) and Pd—C (10%, 6 mg) in ethanol is stirred at room temperature under H$_2$ (H$_2$ balloon) over night. After filtration, the solvent is removed and the residue is purified by preparative TLC to give the title compound. $^1$H NMR (CDCl$_3$) 8.34 (s, 1H), 8.31–8.33 (m, 1H), 7.50–7.55 (m, 1H), 7.23–7.28 (m, 2H), 7.10 (s, 1H), 5.73 (s, 2H), 2.54 (s, 3H), 2.48 (t, 2H), 1.44–1.53 (m, 2H), 0.89 (t, 3H).

Compounds 5–8 Are Prepared via Methods Similar to that Illustrated for the Synthesis of Compound 4.

Compound 5

4-[2-(3-Fluoro-pyridin-2-yl)-imidazol-1-ylmethyl]-5-propyl-pyrimidine

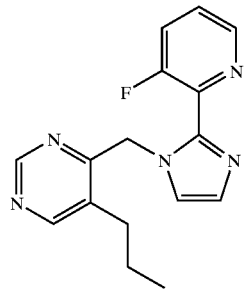

$^1$H-NMR (CDCl$_3$) δ: 8.84 (s, 1H), 8.41 (s, 1H), 8.19–8.21 (m, 1H), 7.42–7.48 (m, 1H), 7.24 (d, 1H), 7.15–7.18 (m, 1H), 7.08 (d, 1H), 5.76 (s, 2H), 2.53 (t, 2H), 1.46–1.58 (m, 2H), 0.89 (t, 3H).

Compound 6

4-[2-(6-Fluoro-pyridin-2-yl)-imidazol-1-ylmethyl]-5-propyl-pyrimidine

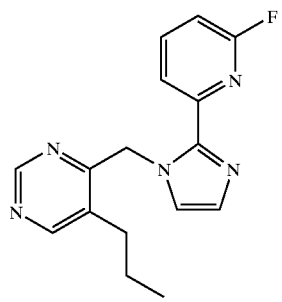

$^1$H-NMR (CDCl$_3$) δ: 8.87 (s, 1H), 8.49 (s, 1H), 8.12 (d, 1H), 7.78 (q, 1H), 7.23 (s, 1H), 7.13 (s, 1H), 6.75 (dd, 1H), 5.96 (s, 2H), 2.76 (t, 2H), 1.62–1.72 (m, 2H), 1.01 (t, 3H).

LC-MS (M+1) 298.2

Compound 7

5-(3-Fluoro-propyl)-4-[2-(3-fluoro-pyridin-2-yl)-imidazol-1-ylmethyl]-pyrimidine

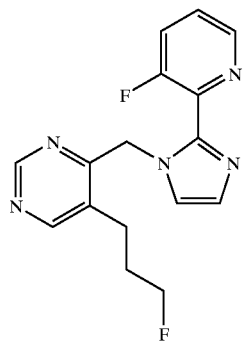

LC-MS (M+1) 316.1 (retention time: 0.63 min).

Compound 8

6-[1-(5-Propyl-pyrimidin-4-ylmethyl)-1H-imidazol-2-yl]-pyridine-2-carbonitrile

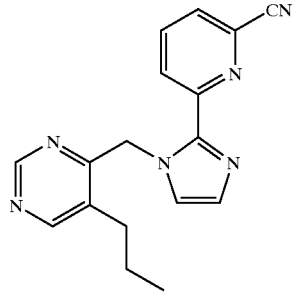

LC-MS (M+1) 305.1 (retention time: 1.01 min).

Compound 9

4-[2-(3-Fluoro-pyridin-2-yl)-imidazol-1-ylmethyl]-5-propyl-6-pyrazol-1-yl-pyrimidine

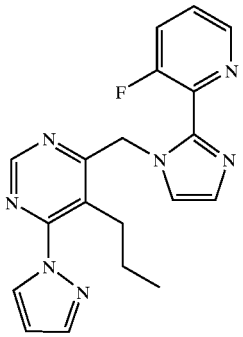

To a suspension of NaH (15 mg, 60% in mineral oil, 0.37 mmol) in anhydrous THF (4 mL), a solution of pyrazole (20 mg, 0.3 mmol) in THF (3 mL) is added dropwise. The mixture is stirred at room temperature for 20 minutes. To the mixture, a solution of 4-chloro-6-[2-(3-fluoro-pyridin-2-yl)-imidazol-1-ylmethyl]-5-propyl-pyrimidine (100 mg, 0.3 mmol) in THF (3 mL) is added. The mixture is stirred at room temperature overnight. The solvent is removed in vacuo. The residue is dissolved in DCM, and the mixture is washed with brine, dried over (MgSO$_4$), filtered, and the solvent is evaporated. The residue is purified by preparative TLC with 10% MeOH/DCM to give the title compound. $^1$H-NMR (CDCl$_3$) δ: 0.95 (t, 3H), 1.55–1.61 (m, 2H), 3.11 (t, 2H), 5.94 (s, 2H), 6.46–6.47 (m, 1H), 7.16 (s, 1H), 7.22 (s, 1H), 7.34 (s, 1H), 7.51 (t, 1H), 7.77 (d, 1H), 8.26 (s, 1H), 8.45 (d, 1H), 8.71 (s, 1H).

Compound 10

4-[2-(3-Fluoro-pyridin-2-yl)-imidazol-1-ylmethyl]-5-propyl-6-pyridin-4-yl-pyrimidine

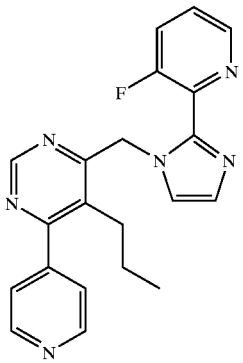

A mixture of 4-chloro-6-[2-(3-fluoro-pyridin-2-yl)-imidazol-1-ylmethyl]-5-propyl-pyrimidine (268 mg, 0.81 mmol), 4-tributylstannanyl-pyridine (1.21 mmol), Pd(PPh$_3$)$_4$ (0.08 mmol, 93 mg) in toluene (10 mL) is degassed. The mixture is then heated at 100° C. overnight. Saturated KF aqueous solution (8 mL) is added and the mixture is stirred for 15 minutes. The layers are separated and the aqueous layer is extracted with EtOAc (10 mL). The combined extracts are washed with brine (15 mL), dried (Na$_2$SO$_4$), and evaporated. Preparative TLC (5% methanol in DCM) purification of the residue provides the title product. $^1$H NMR (CDCl$_3$) 8.95 (s, 1H), 8.65 (d, 1H), 8.26 (d, 1H), 7.77–7.84 (m, 2H), 7.49 (t, 1H), 7.34 (t, 1H), 7.30 (s, 1H), 7.19–7.22 (m, 1H), 7.14 (s, 1H), 5.92 (s, 2H), 2.87–2.91 (m, 2H), 1.46–1.52 (m, 2H), 0.81 (t, 3H).

Compound 11

4-[2-(3-Fluoro-pyridin-2-yl)-imidazol-1-ylmethyl]-5-propyl-6-pyridin-3-yl-pyrimidine

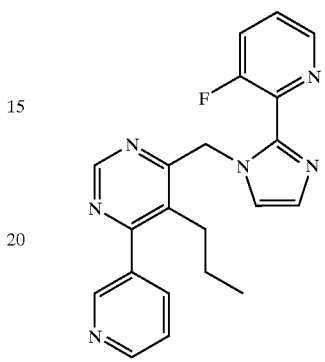

A mixture of 4-chloro-6-[2-(3-fluoro-pyridin-2-yl)-imidazol-1-ylmethyl]-5-propyl-pyrimidine (268 mg, 0.81 mmol), 3-pyridyl boronic acid (1.84 mmol), Pd$_2$(dba)$_3$ (37 mg, 0.04 mmol), (t-Bu)$_3$P (8 mg, 0.04 mmol) and Cs$_2$CO$_3$ (600 mg, 1.84 mmol) in dioxane (6 mL) is degassed. The mixture is then heated at 100° C. for 6 hours. The solvent is removed in vacuo and water (10 mL) and EtOAc (15 mL) is added. The layers are separated and the aqueous layer is extracted with EtOAc (15 mL). The combined extracts are washed with brine (20 mL), dried (Na$_2$SO$_4$), and evaporated. Preparative TLC purification of the residue provides the title product. $^1$H NMR (CDCl$_3$) 8.95 (s, 1H), 8.69 (s, 2H), 8.24 (d, 1H), 7.79 (d, 1H), 7.51 (t, 1H), 7.40–7.43 (m, 1H), 7.32 (s, 1H), 7.21–7.25 (m, 1H), 7.19 (s, 1H), 5.91 (s, 2H), 2.65–2.69 (m, 2H), 1.41–1.47 (m, 2H), 0.81 (t, 3H).

Compounds 12–23 Are Prepared via Methods Similar to Those Illustrated for the Synthesis of Compounds 10 and 11

Compound 12

4-[2-(6-Fluoro-pyridin-2-yl)-imidazol-1-ylmethyl]-6-methyl-5-propyl-pyrimidine

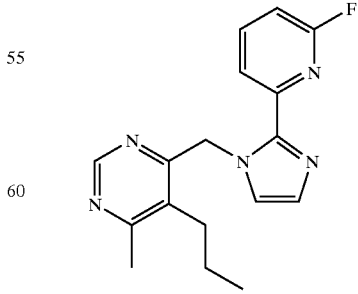

LC-MS (M+1) 312.1 (retention time: 1.01 min).

Compound 13

4-[2-(3-Fluoro-pyridin-2-yl)-imidazol-1-ylmethyl]-5-propyl-6-thiazol-2-yl-pyrimidine

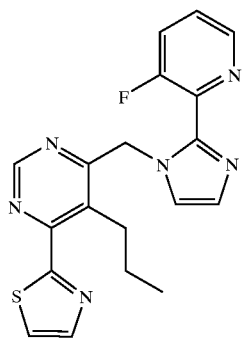

LC-MS (M+1) 381.2 (retention time: 1.10 min).

Compound 14

4-[2-(3-Fluoro-pyridin-2-yl)-imidazol-1-ylmethyl]-5-propyl-6-pyridin-2-yl-pyrimidine

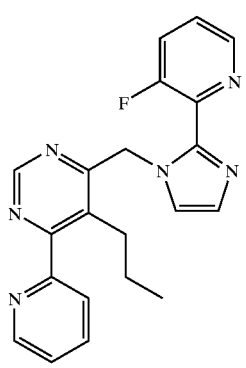

$^1$H NMR (CDCl$_3$) 8.93 (s, 1H), 8.65 (d, 1H), 8.26 (d, 1H), 7.77–7.84 (m, 2H), 7.49 (t, 1H), 7.34 (t, 1H), 7.30 (s, 1H), 7.19–7.22 (m, 1H), 7.14 (s, 1H), 5.92 (s, 2H), 2.87–2.91 (m, 2H), 1.46–1.52 (m, 2H), 0.81 (t, 3H).

Compound 15

4-[2-(3-Fluoro-pyridin-2-yl)-imidazol-1-ylmethyl]-5-propyl-6-pyrazin-2-yl-pyrimidine

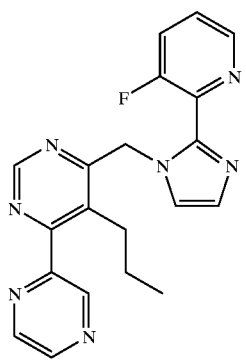

$^1$H NMR (CDCl$_3$) 9.17 (d, 1H), 8.99 (s, 1H), 8.64–8.66 (m, 2H), 8.25 (d, 1H), 7.52 (t, 1H), 7.34 (s, 1H), 7.21–7.25 (m, 1H), 7.17 (s, 1H), 5.96 (s, 2H), 2.90–2.94 (m, 2H), 1.54–1.59 (m, 2H), 0.89 (t, 3H).

Compound 16

4-[2-(3-Fluoro-pyridin-2-yl)-imidazol-1-ylmethyl]-6-methyl-5-propyl-pyrimidine

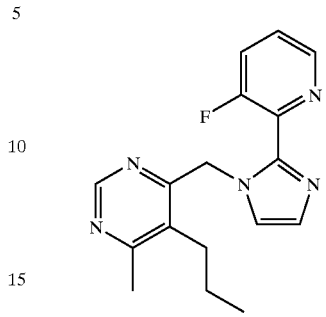

$^1$H NMR (CDCl$_3$) 8.78 (s, 1H), 8.30 (d, 1H), 7.52 (t, 1H), 7.26 (d, 1H), 7.24 (s, 1H), 7.10 (s, 1H), 5.80 (s, 2H), 2.59 (t, 2H), 2.52 (s, 3H), 1.20–1.31 (m, 2H), 0.97 (t, 3H).

Compound 17

6-[1-(6-Methyl-5-propyl-pyrimidin-4-ylmethyl)-1H-imidazol-2-yl]-pyridine-2-carbonitrile

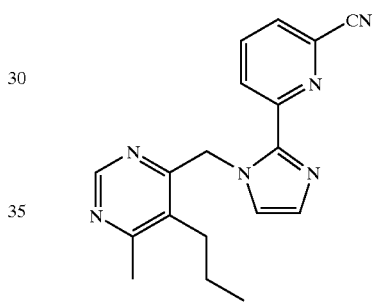

$^1$H NMR (CDCl$_3$) 8.71 (s, 1H), 8.49 (d, 1H), 7.82 (t, 1H), 7.50 (d, 1H), 7.27 (s, 1H), 7.18 (s, 1H), 5.93 (s, 2H), 2.82 (t, 2H), 2.58 (s, 3H), 1.52–1.66 (m, 2H), 1.04 (t, 3H).

Compound 18

5-(3-Fluoro-propyl)-4-[2-(3-fluoro-pyridin-2-yl)-imidazol-1-ylmethyl]-6-methyl-pyrimidine

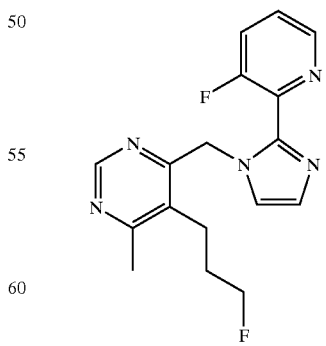

$^1$H NMR (CDCl$_3$) 8.82 (s, 1H), 8.30 (s, 1H), 7.54 (t, 1H), 7.30 (s, 2H), 7.10 (s, 1H), 5.82 (s, 2H), 4.51 (t, 1H), 4.35 (t, 1H), 2.80–2.85 (m, 2H), 2.54 (s, 3H), 1.68–1.86 (m, 2H).

Compound 19

2-[1-(6-Methyl-5-propyl-pyrimidin-4-ylmethyl)-1H-imidazol-2-yl]-thiazole-4-carbonitrile

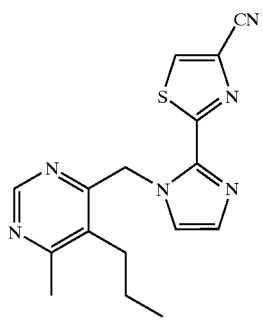

LC-MS (M+1) 325.1 (retention time: 1.13 min).

Compound 20

4-[2-(2,5-Difluoro-phenyl)-imidazol-1-ylmethyl]-5-ethyl-6-methyl-pyrimidine

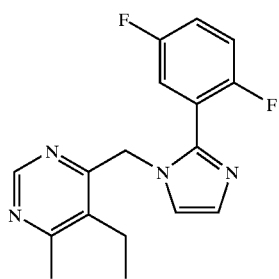

LC-MS (M+1) 315.2 (retention time: 0.99 min).

Compound 21

4-Methyl-5-propyl-6-[2-(6-trifluoromethyl-pyridin-2-yl)-imidazol-1-ylmethyl]-pyrimidine

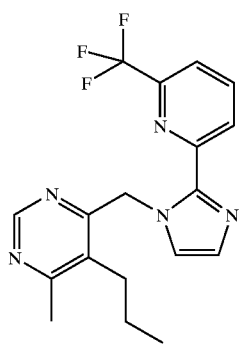

LC-MS (M+1) 362.2 (retention time: 1.13 min).

Compound 22

2-[1-(6-Methyl-5-propyl-pyrimidin-4-ylmethyl)-1H-imidazol-2-yl]-nicotinonitrile

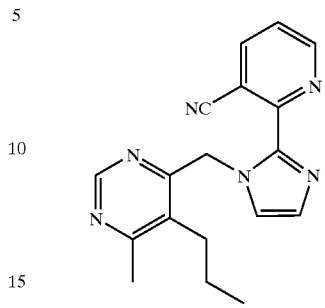

$^1$H NMR (CDCl$_3$) 8.73 (s, 1H), 8.54 (dd, 1H), 8.06 (dd, 1H), 7.32 (s, 1H), 7.24–7.29 (m, 1H), 7.11 (s, 1H), 5.87 (s, 2H), 2.60–2.67 (m, 2H), 2.51 (s, 3H), 1.47–1.55 (m, 2H), 0.99 (t, 3H).

Compound 23

3-[1-(5-Ethyl-6-methyl-pyrimidin-4-ylmethyl)-1H-imidazol-2-yl]-benzonitrile

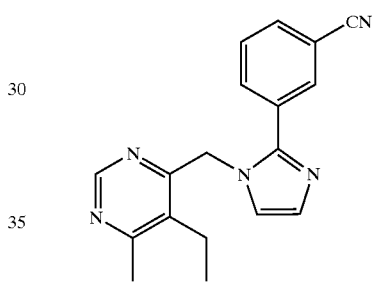

LC-MS (M+1) 304.2 (retention time: 0.92 min).

Compound 24

6-[2-(6-Fluoro-pyridin-2-yl)-imidazol-1-ylmethyl]-5-propyl-pyrimidin-4-ylamine

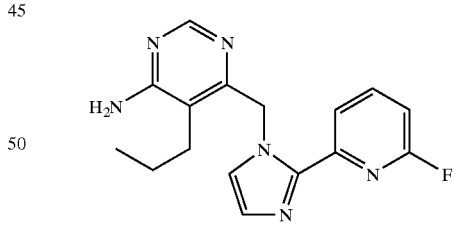

A solution of 6-chloro-4-[2-(6-fluoro-pyridin-2-yl)-imidazol-1-ylmethyl]-5-propyl-pyrimidine (2.25 mmol) and NaN$_3$ (731 mg, 11.25 mmol) in DMF (15 mL) is heated at 70° C. in a sealed tube overnight. The solvent is removed in vacuo and water (10 mL) and EtOAc (10 mL) are added to the residue. The layers are separated and the aqueous layer is extracted with EtOAc (2×10 mL). The combined extracts are washed with brine (15 mL) and dried with Na$_2$SO$_4$. The solvent is removed in vacuo and the resulting yellow oil (6-azido-4-[2-(6-fluoro-pyridin-2-yl)-imidazol-1-ylmethyl]-5-propyl-pyrimidine) is used for the next step without further purification.

Pd/C (10%, 10 mg) is added to a solution of 6-azido-4-[2-(6-fluoro-pyridin-2-yl)-imidazol-1-ylmethyl]-5-propyl-pyrimidine (2 mmol) in MeOH (20 mL). The mixture is stirred under H$_2$ at 30 psi for 4 hours. The catalyst is filtered away and the filtrate is evaporated in vacuo to give the title compound as a yellow solid. $^1$H NMR (CDCl$_3$) 8.35 (s, 1H), 8.12–8.14 (m, 1H), 7.82 (t, 1H), 7.17 (d, 1H), 7.13 (d, 1H), 6.80–6.82 (m, 1H), 5.92 (s, 2H), 4.88 (s, 2H), 2.53–2.57 (m, 2H), 1.48–1.55 (m, 2H), 0.95 (t, 3H).

Compound 25

4-[2-(6-Fluoro-pyridin-2-yl)-imidazol-1-ylmethyl]-6-methoxy-5-propyl-pyrimidine

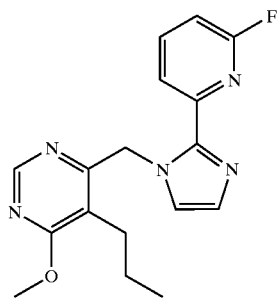

A solution of 6-chloro-4-[2-(6-fluoro-pyridin-2-yl)-imidazol-1-ylmethyl]-5-propyl-pyrimidine (0.23 mmol), sodium methoxide (0.46 mmol) in methanol (5 mL) is stirred at ROOM TEMPERATURE under N$_2$ overnight. Acetic acid (0.23 mmol) is added, followed by water/acetic acetate work-up. On drying, the solvent is removed in vacuo. Preparative TLC separation gives the title compound. LC-MS (M+1) 328.2 (retention time: 1.01 min).

Compound 26

4-[2-(3-Fluoro-pyridin-2-yl)-imidazol-1-ylmethyl]-6-isopropoxy-5-propyl-pyrimidine

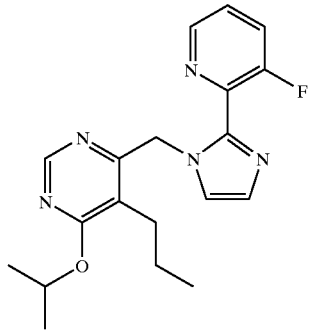

This compound is prepared using a method similar to that described in Example 25. LC-MS (M+1) 356.3 (retention time: 1.12 min).

Compound 27
Ethyl-{6-[2-(6-fluoro-pyridin-2-yl)-imidazol-1-ylmethyl]-5-propyl-pyrimidin-4-yl}-amine

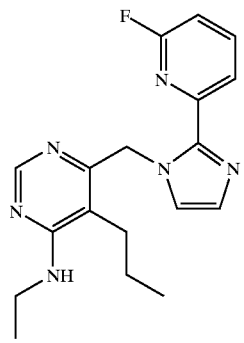

A mixture of 6-chloro-4-[2-(6-fluoro-pyridin-2-yl)-imidazol-1-ylmethyl]-5-propyl-pyrimidine (60 mg, 0.18 mmol) and ethylamine (2M in THF, 2 mL) is heated at 70° C. in a sealed tube overnight. Solvent is removed. Water (10 mL) and ethyl acetate (15 mL) are added. The layers are separated—the aqueous layer is extracted with ethyl acetate (2×20 mL) and the organic layers are combined. On drying, the solvent is removed in vacuo. Preparative TLC separation gives the title compound. LC-MS (M+1) 341.2 (retention time: 1.00 min).

Compounds 28–29 are prepared via a method similar to that illustrated in the synthesis of Compound 27.

Compound 28
Methyl-{6-[2-(3-methylamino-pyridin-2-yl)-imidazol-1-ylmethyl]-5-propyl-pyrimidin-4-yl}-amine

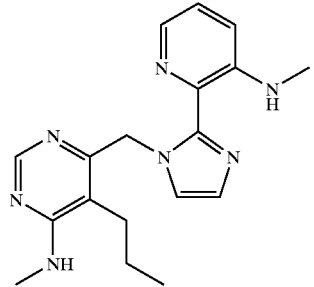

LC-MS (M+1) 338.2 (retention time: 0.96 min).
Compound 29
{6-[2-(6-Fluoro-pyridin-2-yl)-imidazol-1-ylmethyl]-5-propyl-pyrimidin-4-yl}-dimethyl-amine

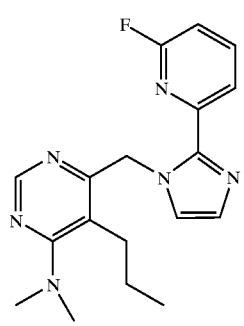

$^1$H NMR (CDCl$_3$) 8.40 (s, 1H), 8.07–8.11 (m, 1H), 7.80 (t, 1H), 7.20 (d, 1H), 7.12 (d, 1H), 6.76–6.80 (m, 1H), 5.87 (s, 2H), 3.00 (s, 6H), 2.69–2.74 (m, 2H), 1.48–1.56 (m, 2H), 0.90 (t, 3H).

Example 3

Ligand Binding Assay

The high affinity of compounds of this invention for the benzodiazepine site of the $GABA_A$ receptor is confirmed using a binding assay essentially described by Thomas and Tallman (1981) *J. Bio. Chem.* 156:9838–9842, and (1983) *J. Neurosci.* 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contain 100 µl of tissue homogenate, 100 µl of radioligand, (0.5 nM $^3$H-RO15-1788 [$^3$H-Flumazenil], specific activity 80 Ci/mmol), and test compound or control (see below), and are brought to a total volume of 500 µl with Buffer A. Incubations are carried out for 30 minutes at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H RO15-1788 with 10 µM Diazepam (Research Biochemicals International, Natick, Mass.). Data are collected in triplicate, averaged, and percent inhibition of total specific binding (Total Specific Binding=Total-Nonspecific) is calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. Each of the compounds set forth above was tested in this fashion and each was found to have a $K_i$ of <1 µM. Preferred compounds of the invention exhibit $K_i$ values of less than 100 nM and more preferred compounds of the invention exhibit $K_i$ values of less than 10 nM.

Example 4

Electrophysiology

The following assay is used to determine if a compound of the invention acts as an agonist, an antagonist, or an inverse agonist at the benzodiazepine site of the $GABA_A$ receptor.

Assays are carried out essentially as described in White and Gurley (NeuroReport 6:1313–1316, 1995) and White, Gurley, Hartnett, Stirling, and Gregory (Receptors and Channels 3:1–5, 1995) with modifications. Electrophysiological recordings are carried out using the two electrode voltage-clamp technique at a membrane holding potential of −70 mV. *Xenopus laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evocable GABA current (e.g., 1 µM–9 µM). Each oocyte is exposed to increasing concentrations of a compound being evaluated (test compound) in order to evaluate a concentration/effect relationship. Test compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 µM RO15-1788, followed by exposure to GABA+1 µM RO15-1788+test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

Example 5

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10$^6$ cells/mL with warm (37° C.) medium (VITACELL Minimum Essential Medium Eagle, ATCC catalog # 30–2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 μL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOP-COUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

What is claimed is:

1. A compound having the formula:

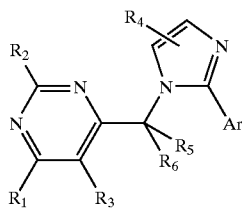

or a pharmaceutically acceptable salt thereof, wherein:

$R_1$ is selected from:
(a) hydrogen, halogen, nitro and cyano; and
(b) groups of the formula:

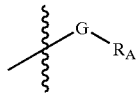

wherein:
G is a bond, $C_1$–$C_8$alkyl, —N($R_B$)—, —O—, —C(=O)—, —C(=O)N($R_B$)—, —N($R_B$)C(=O)—, —S(O)$_m$—, —CH$_2$C(=O)—, —S(O)$_m$N($R_B$)— or —N($R_B$)S(O)$_m$—; wherein m is 0, 1 or 2; and $R_A$ and each $R_B$ are independently selected from:
(a) hydrogen; and
(b) $C_1$–$C_8$alkyl, $C_2$–$C_8$alkenyl, $C_2$–$C_8$alkynyl and 3- to 12-membered carbocycles and heterocycles, each of which is substituted with from 0 to 4 substituents independently selected from halogen, hydroxy, nitro, cyano, amino, $C_1$–$C_4$alkyl, $C_1$–$C_4$alkoxy, $C_1$–$C_4$alkanoyl, mono- and di($C_1$–$C_4$alkyl)amino, $C_1$–$C_4$haloalkyl and $C_1$–$C_4$haloalkoxy;

$R_2$ is hydrogen, halogen, hydroxy, nitro, cyano, amino, $C_1$–$C_4$alkyl, $C_1$–$C_4$haloalkyl, $C_1$–$C_4$alkoxy, $C_1$–$C_4$haloalkoxy, $C_3$–$C_7$cycloalkyl, or mono- or di-($C_1$–$C_4$alkyl)amino;

$R_3$ is hydrogen, halogen, hydroxy, nitro, cyano, amino, $C_1$–$C_8$alkyl, $C_2$–$C_8$alkenyl, $C_2$–$C_8$alkynyl, $C_3$–$C_7$cycloalkyl, $C_1$–$C_8$haloalkyl, $C_1$–$C_8$alkoxy, $C_1$–$C_8$haloalkoxy, $C_2$–$C_8$alkyl ether, $C_2$–$C_8$haloalkyl ether, or mono- or di-($C_1$–$C_8$alkyl)amino;

$R_4$ represents 0, 1 or 2 substituents independently chosen from halogen, hydroxy, nitro, cyano, amino, $C_1$–$C_4$alkyl, $C_1$–$C_4$alkoxy, mono- and di($C_1$–$C_4$alkyl)amino, $C_3$–$C_7$cycloalkyl, $C_1$–$C_2$haloalkyl and $C_1$–$C_2$haloalkoxy;

Ar represents phenyl, naphthyl or 5- to 10-membered heteroaryl, each of which is substituted with from 0 to 4 substituents independently selected from halogen, hydroxy, nitro, cyano, amino, $C_1$–$C_8$alkyl, $C_1$–$C_8$alkenyl, $C_1$–$C_8$alkynyl, $C_3$–$C_7$cycloalkyl ($C_0$–$C_8$alkyl), $C_1$–$C_8$haloalkyl, $C_1$–$C_8$alkoxy, $C_3$–$C_7$cycloalkyl($C_1$–$C_8$alkoxy), $C_1$–$C_8$haloalkoxy, $C_1$–$C_8$alkyl ether, $C_1$–$C_8$alkanone, $C_1$–$C_8$alkanoyl, 3- to 7-membered heterocycloalkyl($C_0$–$C_8$alkyl), oxo, $C_1$–$C_8$hydroxyalkyl, $C_1$–$C_8$aminoalkyl, and mono- and di-($C_1$–$C_8$alkyl)amino($C_0$–$C_8$alkyl); and $R_5$ and $R_6$ are independently hydrogen, halogen, methyl or ethyl.

2. A compound or salt according to claim 1, wherein $R_1$ is selected from:
(a) hydrogen and halogen; and
(b) groups of the formula:

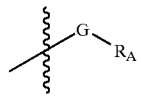

wherein:
(i) G is a bond, —NH—, —N($R_B$)—, —O— or —C(=O)—; and
(ii) $R_A$ and each $R_B$ are independently selected from $C_1$–$C_6$alkyl, $C_2$–$C_6$alkenyl, $C_2$–$C_6$alkynyl, piperidinyl, piperazinyl, morpholinyl, thienyl, pyridyl, pyrimidyl, pyrazolyl, thiazolyl and pyrazinyl, each of which is substituted with from 0 to 4 substituents independently selected from halogen, hydroxy, cyano, amino, $C_1$–$C_2$alkyl, and $C_1$–$C_2$alkoxy.

3. A compound or salt according to claim 2, wherein $R_1$ is:
(a) hydrogen or halogen; or
(b) $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with hydroxy or $C_1$–$C_2$alkoxy.

4. A compound or salt according to claim 1, wherein $R_2$ is hydrogen or $C_1$–$C_4$alkyl.

5. A compound or salt according to claim 4, wherein $R_2$ is hydrogen or $C_1$–$C_4$alkyl.

6. A compound or salt according to claim 1, wherein $R_3$ is hydrogen, halogen, amino, $C_1$–$C_6$alkyl, $C_2$–$C_6$alkenyl, $C_2$–$C_6$alkynyl, $C_3$–$C_7$cycloalkyl, $C_1$–$C_6$haloalkyl, $C_1$–$C_6$alkoxy, $C_1$–$C_6$haloalkoxy, $C_2$–$C_6$alkyl ether, $C_2$–$C_6$haloalkyl ether or mono- or di-($C_1$–$C_6$alkyl)amino.

7. A compound or salt according to claim 6, wherein $R_3$ is hydrogen, $C_1$–$C_4$alkyl, $C_1$–$C_4$haloalkyl, $C_1$–$C_4$alkoxy or mono- or di-($C_1$–$C_4$alkyl)amino.

8. A compound or salt according to claim 1, wherein $R_4$ represents 0, 1 or 2 substituents independently chosen from halogen, hydroxy, methyl, ethyl, methoxy and trifluoromethyl.

9. A compound or salt according to claim 8, wherein $R_4$ represents 0 substituents.

10. A compound or salt according to claim 1, wherein Ar represents phenyl or a 5- or 6-membered heteroaryl, each of which is substituted with from 0 to 4 substituents independently selected from halogen, hydroxy, nitro, cyano, amino, $C_1$–$C_6$alkyl, $C_1$–$C_6$alkenyl, $C_1$–$C_6$alkynyl, $C_1$–$C_6$haloalkyl, $C_1$–$C_6$alkoxy, $C_1$–$C_6$haloalkoxy, $C_3$–$C_7$cycloalkyl($C_0$–$C_6$alkyl), $C_3$–$C_7$cycloalkyl($C_1$–$C_6$alkoxy), 3- to 7-membered heterocycloalkyl($C_0$–$C_8$alkyl), $C_1$–$C_8$aminoalkyl, $C_1$–$C_6$hydroxyalkyl, and mono- and di-($C_1$–$C_6$alkyl)amino($C_0$–$C_6$alkyl).

11. A compound or salt according to claim 10, wherein Ar represents phenyl, thiazolyl, pyrimidyl or pyridyl, each of which is substituted with from 0 to 4 substituents independently selected from halogen, hydroxy, cyano, amino, $C_1$–$C_4$alkyl, $C_1$–$C_4$alkenyl, $C_1$–$C_4$alkynyl, $C_1$–$C_4$haloalkyl, $C_1$–$C_4$alkoxy, $C_1$–$C_4$haloalkoxy and mono- and di-($C_1$–$C_4$alkyl)amino($C_0$–$C_4$alkyl).

12. A compound or salt according to claim 11, wherein Ar represents phenyl, thiazolyl, or pyridyl, each of which is substituted with from 0 to 3 substituents independently chosen from chloro, fluoro, cyano, amino, $C_1$–$C_4$alkyl, $C_1$–$C_4$alkoxy, $C_1$–$C_2$alkylamino, $C_1$–$C_2$haloalkyl and $C_1$–$C_2$haloalkoxy.

13. A compound or salt according to claim 12, wherein Ar represents phenyl or 2-pyridyl, each of which is substituted with 1, 2 or 3 substituents independently chosen from fluoro, chloro, cyano, trifluoromethyl and methyl.

14. A compound or salt according to claim 1, wherein:
$R_1$ is:
(a) hydrogen or halogen; or
(b) $C_1$–$C_6$alkyl, $C_2$–$C_6$alkenyl, $C_2$–$C_6$alkynyl, $C_1$–$C_6$alkoxy, thienyl, pyridyl, pyrazoly thiazolyl or pyrimidinyl, each of which is unsubstituted or substituted with halogen, hydroxy or $C_1$–$C_2$alkoxy;

$R_2$ is hydrogen, halogen or $C_1$–$C_4$alkyl;

$R_3$ is hydrogen, $C_1$–$C_4$alkyl, $C_1$–$C_4$haloalkyl, $C_1$–$C_4$alkoxy, or mono- or di-($C_1$–$C_4$alkyl)amino;

$R_4$ represents 0, 1 or 2 substituents independently chosen from halogen, hydroxy, methyl, ethyl, methoxy and trifluoromethyl; and Ar represents phenyl, thiazolyl, or pyridyl, each of which is substituted with from 0 to 3 substituents independently chosen from chloro, fluoro, cyano, amino, $C_1$–$C_4$alkyl, $C_1$–$C_4$alkoxy, $C_1$–$C_2$alkylamino, $C_1$–$C_2$haloalkyl and $C_1$–$C_2$haloalkoxy.

15. A compound or salt according to claim 1, wherein the compound has the formula:

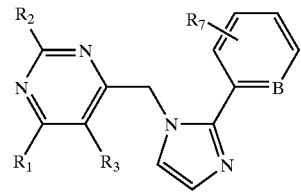

wherein:
B is CH or N;
$R_1$ is (a) hydrogen or halogen; or (b) $C_1$–$C_6$alkyl, $C_2$–$C_6$alkenyl, $C_2$–$C_6$alkynyl, $C_1$–$C_6$alkoxy, thienyl, pyridyl, pyrazolyl, thiazolyl or pyrimidinyl, each of which is unsubstituted or substituted with halogen, hydroxy or $C_1$–$C_2$alkoxy;
$R_2$ is hydrogen, halogen or methyl;
$R_3$ is hydrogen, $C_1$–$C_4$alkyl, $C_1$–$C_4$haloalkyl, $C_1$–$C_4$alkoxy, or mono- or di-($C_1$–$C_4$alkyl)amino; and
$R_7$ represents from 0 to 3 substituents independently chosen from halogen, cyano, $C_1$–$C_4$alkyl, $C_1$–$C_4$alkoxy and $C_1$–$C_4$haloalkyl.

16. A compound or salt according to claim 15, wherein $R_1$ is hydrogen, halogen, methyl or methoxy.

17. A compound or salt according to claim 15, wherein $R_1$ is pyridyl, pyrazolyl or thiazolyl.

18. A compound or salt according to claim 1, wherein the compound is selected from:

{6-[2-(6-fluoro-pyridin-2-yl)-imidazol-1-ylmethyl]-5-propyl-pyrimidin-4-yl}-dimethyl-amine;
2-[1-(6-methyl-5-propyl-pyrimidin-4-ylmethyl)-1H-imidazol-2-yl]-nicotinonitrile;
2-[1-(6-methyl-5-propyl-pyrimidin-4-ylmethyl)-1H-imidazol-2-yl]-thiazole-4-carbonitrile;
3-[1-(5-ethyl-6-methyl-pyrimidin-4-ylmethyl)-1H-imidazol-2-yl]-benzonitrile;
4-[2-(2,5-difluoro-phenyl)-imidazol-1-ylmethyl]-5-ethyl-6-methyl-pyrimidine;
4-[2-(3-fluoro-pyridin-2-yl)-imidazol-1-ylmethyl]-2-methyl-5-propyl-pyrimidine;
4-[2-(3-fluoro-pyridin-2-yl)-imidazol-1-ylmethyl]-5-propyl-6-pyrazol-1-yl-pyrimidine;
4-[2-(3-fluoro-pyridin-2-yl)-imidazol-1-ylmethyl]-5-propyl-6-pyrazin-2-yl-pyrimidine;
4-[2-(3-fluoro-pyridin-2-yl)-imidazol-1-ylmethyl]-5-propyl-6-pyridin-4-yl-pyrimidine;
4-[2-(3-fluoro-pyridin-2-yl)-imidazol-1-ylmethyl]-5-propyl-6-pyridin-3-yl-pyrimidine;
4-[2-(3-fluoro-pyridin-2-yl)-imidazol-1-ylmethyl]-5-propyl-6-pyridin-2-yl-pyrimidine;
4-[2-(3-fluoro-pyridin-2-yl)-imidazol-1-ylmethyl]-5-propyl-6-thiazol-2-yl-pyrimidine;
4-[2-(3-fluoro-pyridin-2-yl)-imidazol-1-ylmethyl]-5-propyl-pyrimidine;
4-[2-(3-fluoro-pyridin-2-yl)-imidazol-1-ylmethyl]-6-isopropoxy-5-propyl-pyrimidine;
4-[2-(3-fluoro-pyridin-2-yl)-imidazol-1-ylmethyl]-6-methyl-5-propyl-pyrimidine;
4-[2-(6-fluoro-pyridin-2-yl)-imidazol-1-ylmethyl]-5-propyl-pyrimidine;
4-[2-(6-fluoro-pyridin-2-yl)-imidazol-1-ylmethyl]-6-methoxy-5-propyl-pyrimidine;
4-[2-(6-fluoro-pyridin-2-yl)-imidazol-1-ylmethyl]-6-methyl-5-propyl-pyrimidine;
4-chloro-6-[2-(3-fluoro-pyridin-2-yl)-imidazol-1-ylmethyl]-2-methyl-5-propyl-pyrimidine;

4-chloro-6-[2-(3-fluoro-pyridin-2-yl)-imidazol-1-ylmethyl]-5-propyl-pyrimidine;
4-chloro-6-[2-(6-fluoro-pyridin-2-yl)-imidazol-1-ylmethyl]-2-methyl-5-propyl-pyrimidine;
4-methyl-5-propyl-6-[2-(6-trifluoromethyl-pyridin-2-yl)-imidazol-1-ylmethyl]-pyrimidine;
5-(3-fluoro-propyl)-4-[2-(3-fluoro-pyridin-2-yl)-imidazol-1-ylmethyl]-pyrimidine;
5-(3-fluoro-propyl)-4-[2-(3-fluoro-pyridin-2-yl)-imidazol-1-ylmethyl]-6-methyl-pyrimidine;
6-[1-(5-propyl-pyrimidin-4-ylmethyl)-1H-imidazol-2-yl]-pyridine-2-carbonitrile;
6-[1-(6-methyl-5-propyl-pyrimidin-4-ylmethyl)-1H-imidazol-2-yl]-pyridine-2-carbonitrile;
6-[2-(6-fluoro-pyridin-2-yl)-imidazol-1-ylmethyl]-5-propyl-pyrimidin-4-ylamine;
ethyl-{6-[2-(6-fluoro-pyridin-2-yl)-imidazol-1-ylmethyl]-5-propyl-pyrimidin-4-yl}-amine; and
methyl-{6-[2-(3-methylamino-pyridin-2-yl)-imidazol-1-ylmethyl]-5-propyl-pyrimidin-4-yl}-amine.

19. A pharmaceutical composition comprising a compound or salt according to claim 1 in combination with a physiologically acceptable carrier or excipient.

20. A pharmaceutical composition according to claim 22, wherein the pharmaceutical composition is formulated as an injectible fluid, an aerosol, a cream, a gel, a pill, a capsule, a syrup or a transdermal patch.

21. A method for the treatment of anxiety, depression, or a sleep disorder, comprising administering to a patient in need of such treatment a $GABA_A$ receptor modulatory amount of a compound or salt according to claim 1.

22. A method for determining the presence or absence of $GABA_A$ receptor in a sample, comprising the steps of:
(a) contacting a sample with a compound or salt according claim 1, under conditions that permit binding of the compound to $GABA_A$ receptor;
(b) removing the compound or salt that is not bound to $GABA_A$ receptor; and
(c) detecting a level of the compound or salt bound to $GABA_A$ receptor;
and therefrom determining the presence or absence of $GABA_A$ receptor in the sample.

23. A method according to claim 22, wherein the presence or absence of bound compound is detected using autoradiography.

24. A packaged pharmaceutical preparation comprising a pharmaceutical composition according to claim 19 in a container and instructions for using the composition to treat a patient suffering from anxiety, depression, or a sleep disorder.

* * * * *